US012258617B2

(12) United States Patent
Spurlock, III

(10) Patent No.: US 12,258,617 B2
(45) **Date of Patent: *Mar. 25, 2025**

(54) LONG NON-CODING RNA GENE EXPRESSION SIGNATURES IN DISEASE MONITORING AND TREATMENT

(71) Applicant: DECODE HEALTH, INC., Nashville, TN (US)

(72) Inventor: Charles Floyd Spurlock, III, Nashville, TN (US)

(73) Assignee: Decode Health, Inc., Nashville, TN (US)

(*) Notice: Subject to any disclaimer, the term of this patent is extended or adjusted under 35 U.S.C. 154(b) by 54 days.

This patent is subject to a terminal disclaimer.

(21) Appl. No.: 17/234,164

(22) Filed: Apr. 19, 2021

(65) Prior Publication Data

US 2022/0112541 A1 Apr. 14, 2022

Related U.S. Application Data

(63) Continuation of application No. 16/153,028, filed on Oct. 5, 2018, now Pat. No. 10,982,259.

(60) Provisional application No. 62/568,737, filed on Oct. 5, 2017.

(51) Int. Cl.

| | |
|---|---|
| ***C07H 21/02*** | (2006.01) |
| ***C12N 15/11*** | (2006.01) |
| ***C12N 15/113*** | (2010.01) |
| ***C12Q 1/6809*** | (2018.01) |
| ***C12Q 1/6883*** | (2018.01) |

(52) U.S. Cl.
CPC .......... *C12Q 1/6809* (2013.01); *C12N 15/111* (2013.01); *C12N 15/113* (2013.01); *C12Q 1/6883* (2013.01); *C12Q 2600/106* (2013.01); *C12Q 2600/118* (2013.01); *C12Q 2600/158* (2013.01)

(58) Field of Classification Search
CPC .......................... C12N 15/113; A61K 2300/00
See application file for complete search history.

(56) References Cited

U.S. PATENT DOCUMENTS

2013/0178428 A1* 7/2013 Hoon .................. C12Q 1/6886 514/19.3

OTHER PUBLICATIONS

Santoro et al. (J Mol Neurosci, 2016, 59, 18-23).*
Han et al. (Tumor Biol, 201637, 6847-6854).*
Quagliata et al. (Hepatology, 2014, vol. 59, No. 3, 911-923).*

* cited by examiner

*Primary Examiner* — Amy Rose Hudson
(74) *Attorney, Agent, or Firm* — Baker, Donelson, Bearman, Caldwell & Berkowitz, P.C.; Dominic A. Rota; Wesley M. Barbee

(57) ABSTRACT

Differential expression of long non-coding RNAs (lncRNAs) and enhancer RNAs (eRNAs) are used to monitor diseases and determine therapeutic efficacy in, for example, neurological diseases, inflammatory diseases, rheumatic diseases, and autoimmune diseases. Machine learning systems are used to identify lncRNAs or eRNAs having differential expression correlated with responsiveness to various therapies.

7 Claims, 14 Drawing Sheets

Specification includes a Sequence Listing.

| | BINARY COMPARISONS | | | | |
|---|---|---|---|---|---|
| PATIENT | CTRL vs. CIS-MS | CTRL vs. MS-NAÏVE | CTRL vs. MS-EST | CTRL vs. OND-I | CIS-MS vs. OND-I |
| CTRL #1 | CTRL | CTRL | CTRL | CTRL | CIS-MS |
| CIS-MS #1 | CIS-MS | MS-NAÏVE | MS-EST | OND-I | CIS-MS |

| | | mRNA | | | | lncRNA | | | |
|---|---|---|---|---|---|---|---|---|---|
| | | RATIOSCORE | | VALIDATION | | RATIOSCORE | | VALIDATION | |
| CASE | CONTROL | Ratios | Accuracy | Accuracy | ROC | Ratios | Accuracy | Accuracy | ROC |
| CTRL | CTRL-UFM | 50 | 65.7 | 87.7 | 0.89 | 38 | 95.2 | 97.1 | 0.97 |
| CTRL | CIS-MS | 38 | 77.6 | 82.7 | 0.69 | 15 | 92.7 | 88.6 | 0.79 |
| CTRL | MS-NAÏVE | 38 | 90.0 | 91.7 | 0.89 | 21 | 88.3 | 89.8 | 0.87 |
| CTRL | MS-EST | 73 | 76.4 | 79.2 | 0.79 | 52 | 92.5 | 77.6 | 0.77 |
| CTRL | OND-I | 47 | 89.6 | 86.0 | 0.88 | 28 | 97.8 | 89.3 | 0.87 |
| CTRL | OND-NI | 40 | 86.2 | 89.0 | 0.88 | 36 | 93.0 | 86.4 | 0.87 |
| CTRL-UFM | CIS-MS | 25 | 98.7 | 92.1 | 0.91 | 14 | 87.8 | 93.5 | 0.89 |
| CTRL-UFM | MS-NAÏVE | 23 | 94.4 | 98.5 | 0.99 | 21 | 83.3 | 92.2 | 0.91 |
| CTRL-UFM | MS-EST | 37 | 98.4 | 99.1 | 0.99 | 36 | 96.2 | 91.3 | 0.92 |
| CTRL-UFM | OND-I | 27 | 97.6 | 97.3 | 0.95 | 21 | 95.5 | 91.4 | 0.91 |
| CTRL-UFM | OND-NI | 22 | 99.1 | 97.3 | 0.97 | 25 | 96.0 | 91.8 | 0.91 |
| CIS-MS | MS-NAÏVE | 32 | 87.8 | 75.6 | 0.75 | 21 | 100.0 | 82.0 | 0.82 |
| CIS-MS | MS-EST | 42 | 98.0 | 86.6 | 0.73 | 41 | 99.2 | 86.5 | 0.80 |
| CIS-MS | OND-I | 29 | 80.3 | 76.0 | 0.75 | 13 | 100.0 | 90.6 | 0.88 |
| CIS-MS | OND-NI | 24 | 96.1 | 91.7 | 0.90 | 14 | 100.0 | 94.3 | 0.93 |
| MS-NAÏVE | MS-EST | 48 | 98.8 | 89.4 | 0.89 | 27 | 99.2 | 91.1 | 0.92 |
| MS-NAÏVE | OND-I | 35 | 88.9 | 90.2 | 0.90 | 20 | 100.0 | 83.8 | 0.85 |
| MS-NAÏVE | OND-NI | 20 | 97.8 | 96.1 | 0.96 | 23 | 99.0 | 92.5 | 0.91 |
| MS-EST | OND-I | 54 | 84.3 | 77.7 | 0.76 | 23 | 96.6 | 94.6 | 0.93 |
| MS-EST | OND-NI | 58 | 94.1 | 83.7 | 0.84 | 30 | 82.0 | 91.4 | 0.92 |
| OND-I | OND-NI | 45 | 96.0 | 88.3 | 0.89 | 26 | 95.0 | 93.6 | 0.93 |

FIG. 11

| Optimized Multi-category Classification Results | | | | | | |
|---|---|---|---|---|---|---|
| | mRNA | | | lncRNA | | |
| Class | Accuracy | Sensitivity | Specificity | Accuracy | Sensitivity | Specificity |
| Multiple sclerosis | .94 | .97 | .90 | .95 | .98 | .92 |
| Other neurologic diseases *inflammatory* | .95 | .92 | .99 | .98 | .98 | .97 |
| Other neurologic diseases *non-inflammatory* | .95 | .91 | .99 | .98 | .98 | .99 |

FIG. 18

SEQUENCE LISTING

<160> NUMBER OF SEQ ID NOS: 92

<210> SEQ ID NO 1
<211> LENGTH: 20
<212> TYPE: DNA
<213> ORGANISM: Homo sapiens

<400> SEQUENCE: 1
aaggcacaga gccaagaagt 20

<210> SEQ ID NO 2
<211> LENGTH: 20
<212> TYPE: DNA
<213> ORGANISM: Homo sapiens

<400> SEQUENCE: 2
cagtgcccag agctatgctt 20

<210> SEQ ID NO 3
<211> LENGTH: 19
<212> TYPE: DNA
<213> ORGANISM: Homo sapiens

<400> SEQUENCE: 3
ggttgtcagg ggataggag 19

<210> SEQ ID NO 4
<211> LENGTH: 20
<212> TYPE: DNA
<213> ORGANISM: Homo sapiens

<400> SEQUENCE: 4
ctgtcaccac cattgagcac 20

<210> SEQ ID NO 5
<211> LENGTH: 20
<212> TYPE: DNA
<213> ORGANISM: Homo sapiens

<400> SEQUENCE: 5
ggggaccaaa aactgtcaga 20

<210> SEQ ID NO 6
<211> LENGTH: 21
<212> TYPE: DNA
<213> ORGANISM: Homo sapiens

<400> SEQUENCE: 6
gcatgatcaa atcatcccct a 21

-continued

<210> SEQ ID NO 7
<211> LENGTH: 20
<212> TYPE: DNA
<213> ORGANISM: Homo sapiens

<400> SEQUENCE: 7
ctggcctctg acatgaacaa 20

<210> SEQ ID NO 8
<211> LENGTH: 20
<212> TYPE: DNA
<213> ORGANISM: Homo sapiens

<400> SEQUENCE: 8
agctgcccat tgcatctatt 20

<210> SEQ ID NO 9
<211> LENGTH: 18
<212> TYPE: DNA
<213> ORGANISM: Homo sapiens

<400> SEQUENCE: 9
atccacaggg gtcacagc 18

<210> SEQ ID NO 10
<211> LENGTH: 18
<212> TYPE: DNA
<213> ORGANISM: Homo sapiens

<400> SEQUENCE: 10
gagggccaat gggaactt 18

<210> SEQ ID NO 11
<211> LENGTH: 20
<212> TYPE: DNA
<213> ORGANISM: Homo sapiens

<400> SEQUENCE: 11
ggcaggacca cagtgatgat 20

<210> SEQ ID NO 12
<211> LENGTH: 20
<212> TYPE: DNA
<213> ORGANISM: Homo sapiens

<400> SEQUENCE: 12
caattcgcca tgtctctctg 20

<210> SEQ ID NO 13
<211> LENGTH: 20
<212> TYPE: DNA
<213> ORGANISM: Homo sapiens

<400> SEQUENCE: 13
gcattaagga gcccacagag 20

<210> SEQ ID NO 14
<211> LENGTH: 20
<212> TYPE: DNA
<213> ORGANISM: Homo sapiens

<400> SEQUENCE: 14
acctggctcc acctcctact 20

-continued

<210> SEQ ID NO 15
<211> LENGTH: 20
<212> TYPE: DNA
<213> ORGANISM: Homo sapiens

<400> SEQUENCE: 15
gaggttggag gatcacttgg 20

<210> SEQ ID NO 16
<211> LENGTH: 20
<212> TYPE: DNA
<213> ORGANISM: Homo sapiens

<400> SEQUENCE: 16
tctgggtggg ttcatttctc 20

<210> SEQ ID NO 17
<211> LENGTH: 21
<212> TYPE: DNA
<213> ORGANISM: Homo sapiens

<400> SEQUENCE: 17
ttcttttcaa agtcgtgtgg a 21

<210> SEQ ID NO 18
<211> LENGTH: 20
<212> TYPE: DNA
<213> ORGANISM: Homo sapiens

<400> SEQUENCE: 18
tggatggaaa attgtgagca 20

<210> SEQ ID NO 19
<211> LENGTH: 20
<212> TYPE: DNA
<213> ORGANISM: Homo sapiens

<400> SEQUENCE: 19
cgcctcagcc ttctaaagtg 20

<210> SEQ ID NO 20
<211> LENGTH: 20
<212> TYPE: DNA
<213> ORGANISM: Homo sapiens

<400> SEQUENCE: 20
actctccaga gtggcaccag 20

<210> SEQ ID NO 21
<211> LENGTH: 20
<212> TYPE: DNA
<213> ORGANISM: Homo sapiens

<400> SEQUENCE: 21
tcacgattca gtcgcaattc 20

<210> SEQ ID NO 22
<211> LENGTH: 20
<212> TYPE: DNA
<213> ORGANISM: Homo sapiens

<400> SEQUENCE: 22

-continued cacagagcag ggcataatga 20

<210> SEQ ID NO 23
<211> LENGTH: 20
<212> TYPE: DNA
<213> ORGANISM: Homo sapiens

<400> SEQUENCE: 23
tgctcatgga gcagaatcag 20

<210> SEQ ID NO 24
<211> LENGTH: 20
<212> TYPE: DNA
<213> ORGANISM: Homo sapiens

<400> SEQUENCE: 24
tcttcccacc aggaaatcac 20

<210> SEQ ID NO 25
<211> LENGTH: 20
<212> TYPE: DNA
<213> ORGANISM: Homo sapiens

<400> SEQUENCE: 25
tcacccacta ccctctcctg 20

<210> SEQ ID NO 26
<211> LENGTH: 20
<212> TYPE: DNA
<213> ORGANISM: Homo sapiens

<400> SEQUENCE: 26
tgaaatgtgg cattcctacg 20

<210> SEQ ID NO 27
<211> LENGTH: 20
<212> TYPE: DNA
<213> ORGANISM: Homo sapiens

<400> SEQUENCE: 27
catggggcta tttggagaaa 20

<210> SEQ ID NO 28
<211> LENGTH: 20
<212> TYPE: DNA
<213> ORGANISM: Homo sapiens

<400> SEQUENCE: 28
caccactggt tcctggctat 20

<210> SEQ ID NO 29
<211> LENGTH: 20
<212> TYPE: DNA
<213> ORGANISM: Homo sapiens

<400> SEQUENCE: 29
gggcttgaac tttggttctg 20

<210> SEQ ID NO 30
<211> LENGTH: 20
<212> TYPE: DNA
<213> ORGANISM: Homo sapiens

<400> SEQUENCE: 30

-continued gttggggagg agcctatgat 20

<210> SEQ ID NO 31
<211> LENGTH: 23
<212> TYPE: DNA
<213> ORGANISM: Homo sapiens

<400> SEQUENCE: 31
ctggaaaatt gaaagaacag aca 23

<210> SEQ ID NO 32
<211> LENGTH: 24
<212> TYPE: DNA
<213> ORGANISM: Homo sapiens

<400> SEQUENCE: 32
ttctttttcc ttatgctatg ttgc 24

<210> SEQ ID NO 33
<211> LENGTH: 22
<212> TYPE: DNA
<213> ORGANISM: Homo sapiens

<400> SEQUENCE: 33
ccacgtgtat caagagacat ca 22

<210> SEQ ID NO 34
<211> LENGTH: 20
<212> TYPE: DNA
<213> ORGANISM: Homo sapiens

<400> SEQUENCE: 34
tttgatgccc ttatcattcc 20

<210> SEQ ID NO 35
<211> LENGTH: 22
<212> TYPE: DNA
<213> ORGANISM: Homo sapiens

<400> SEQUENCE: 35
tggatatttg gtctgcgtag tg 22

<210> SEQ ID NO 36
<211> LENGTH: 20
<212> TYPE: DNA
<213> ORGANISM: Homo sapiens

<400> SEQUENCE: 36
caggctggtc tcaaagtcct 20

<210> SEQ ID NO 37
<211> LENGTH: 20
<212> TYPE: DNA
<213> ORGANISM: Homo sapiens

<400> SEQUENCE: 37
gagaatgctc ctgcctcatc 20

<210> SEQ ID NO 38
<211> LENGTH: 20
<212> TYPE: DNA
<213> ORGANISM: Homo sapiens

<400> SEQUENCE: 38
ccaggtgcac aaagaaatca 20

<210> SEQ ID NO 39
<211> LENGTH: 20
<212> TYPE: DNA
<213> ORGANISM: Homo sapiens

<400> SEQUENCE: 39
tgcggctgga ggagttaata 20

<210> SEQ ID NO 40
<211> LENGTH: 20
<212> TYPE: DNA
<213> ORGANISM: Homo sapiens

<400> SEQUENCE: 40
cgcctctctc ttcctgtctc 20

<210> SEQ ID NO 41
<211> LENGTH: 20
<212> TYPE: DNA
<213> ORGANISM: Homo sapiens

<400> SEQUENCE: 41
cttccctcgt ttctttgctg 20

<210> SEQ ID NO 42
<211> LENGTH: 20
<212> TYPE: DNA
<213> ORGANISM: Homo sapiens

<400> SEQUENCE: 42
acctctcctg gccctatgat 20

<210> SEQ ID NO 43
<211> LENGTH: 20
<212> TYPE: DNA
<213> ORGANISM: Homo sapiens

<400> SEQUENCE: 43
gaacagggga agggagaaag 20

<210> SEQ ID NO 44
<211> LENGTH: 20
<212> TYPE: DNA
<213> ORGANISM: Homo sapiens

<400> SEQUENCE: 44
gccaccaaag gctataccaa 20

<210> SEQ ID NO 45
<211> LENGTH: 20
<212> TYPE: DNA
<213> ORGANISM: Homo sapiens

<400> SEQUENCE: 45
caggaagaag tgcatgttgg 20

<210> SEQ ID NO 46
<211> LENGTH: 19
<212> TYPE: DNA
<213> ORGANISM: Homo sapiens

<400> SEQUENCE: 46
agagctctgg gagggacac 19

<210> SEQ ID NO 47
<211> LENGTH: 20
<212> TYPE: DNA
<213> ORGANISM: Homo sapiens

<400> SEQUENCE: 47
cccaggggtc tgataattca 20

<210> SEQ ID NO 48
<211> LENGTH: 20
<212> TYPE: DNA
<213> ORGANISM: Homo sapiens

<400> SEQUENCE: 48
atgcataggg gacgaaaaca 20

<210> SEQ ID NO 49
<211> LENGTH: 20
<212> TYPE: DNA
<213> ORGANISM: Homo sapiens

<400> SEQUENCE: 49
ctttgcccca cctttaaaca 20

<210> SEQ ID NO 50
<211> LENGTH: 20
<212> TYPE: DNA
<213> ORGANISM: Homo sapiens

<400> SEQUENCE: 50
atagcatgtg atggggcttc 20

<210> SEQ ID NO 51
<211> LENGTH: 23
<212> TYPE: DNA
<213> ORGANISM: Homo sapiens

<400> SEQUENCE: 51
aagctatgtg aagcattttg agc 23

<210> SEQ ID NO 52
<211> LENGTH: 20
<212> TYPE: DNA
<213> ORGANISM: Homo sapiens

<400> SEQUENCE: 52
ccagccaagg tctcctcttt 20

<210> SEQ ID NO 53
<211> LENGTH: 20
<212> TYPE: DNA
<213> ORGANISM: Homo sapiens

<400> SEQUENCE: 53
cctgtagtcc ctccaagcag 20

<210> SEQ ID NO 54
<211> LENGTH: 20
<212> TYPE: DNA

-continued

<213> ORGANISM: Homo sapiens

<400> SEQUENCE: 54
gctgtgtgtt ccaggtgaga 20

<210> SEQ ID NO 55
<211> LENGTH: 20
<212> TYPE: DNA
<213> ORGANISM: Homo sapiens

<400> SEQUENCE: 55
caatggctgt ttcatcctca 20

<210> SEQ ID NO 56
<211> LENGTH: 21
<212> TYPE: DNA
<213> ORGANISM: Homo sapiens

<400> SEQUENCE: 56
ccttactggg tgacaggaaa a 21

<210> SEQ ID NO 57
<211> LENGTH: 20
<212> TYPE: DNA
<213> ORGANISM: Homo sapiens

<400> SEQUENCE: 57
ttttgtgctt ctctgccaag 20

<210> SEQ ID NO 58
<211> LENGTH: 22
<212> TYPE: DNA
<213> ORGANISM: Homo sapiens

<400> SEQUENCE: 58
tgtgtgcaaa ctaagtgcca at 22

<210> SEQ ID NO 59
<211> LENGTH: 20
<212> TYPE: DNA
<213> ORGANISM: Homo sapiens

<400> SEQUENCE: 59
tggcttggag aaaggagaga 20

<210> SEQ ID NO 60
<211> LENGTH: 20
<212> TYPE: DNA
<213> ORGANISM: Homo sapiens

<400> SEQUENCE: 60
ggcaaaagga agtccattca 20

<210> SEQ ID NO 61
<211> LENGTH: 20
<212> TYPE: DNA
<213> ORGANISM: Homo sapiens

<400> SEQUENCE: 61
ttttcccaaa tcccaatcaa 20

<210> SEQ ID NO 62
<211> LENGTH: 20

-continued

<212> TYPE: DNA
<213> ORGANISM: Homo sapiens

<400> SEQUENCE: 62
acaaccgggg ttcttttacc 20

<210> SEQ ID NO 63
<211> LENGTH: 20
<212> TYPE: DNA
<213> ORGANISM: Homo sapiens

<400> SEQUENCE: 63
ggtggaaacc tgacaaatgg 20

<210> SEQ ID NO 64
<211> LENGTH: 20
<212> TYPE: DNA
<213> ORGANISM: Homo sapiens

<400> SEQUENCE: 64
ccaggaaggt cagattccaa 20

<210> SEQ ID NO 65
<211> LENGTH: 20
<212> TYPE: DNA
<213> ORGANISM: Homo sapiens

<400> SEQUENCE: 65
gctgggtacg gtaaaggaca 20

<210> SEQ ID NO 66
<211> LENGTH: 20
<212> TYPE: DNA
<213> ORGANISM: Homo sapiens

<400> SEQUENCE: 66
ctgggaaagg aacacctgaa 20

<210> SEQ ID NO 67
<211> LENGTH: 20
<212> TYPE: DNA
<213> ORGANISM: Homo sapiens

<400> SEQUENCE: 67
ggttgaggcc actgctttac 20

<210> SEQ ID NO 68
<211> LENGTH: 20
<212> TYPE: DNA
<213> ORGANISM: Homo sapiens

<400> SEQUENCE: 68
cccagctgaa gagattggaa 20

<210> SEQ ID NO 69
<211> LENGTH: 20
<212> TYPE: DNA
<213> ORGANISM: Homo sapiens

<400> SEQUENCE: 69
tttccctgtg tcttccatcc 20

<210> SEQ ID NO 70

-continued

<211> LENGTH: 20
<212> TYPE: DNA
<213> ORGANISM: Homo sapiens

<400> SEQUENCE: 70
aaaagctgca gaagccagag 20

<210> SEQ ID NO 71
<211> LENGTH: 20
<212> TYPE: DNA
<213> ORGANISM: Homo sapiens

<400> SEQUENCE: 71
tttttcttgg atgcctggac 20

<210> SEQ ID NO 72
<211> LENGTH: 20
<212> TYPE: DNA
<213> ORGANISM: Homo sapiens

<400> SEQUENCE: 72
atctctccct ccccaagtgt 20

<210> SEQ ID NO 73
<211> LENGTH: 20
<212> TYPE: DNA
<213> ORGANISM: Homo sapiens

<400> SEQUENCE: 73
tgcccacact gtttattgct 20

<210> SEQ ID NO 74
<211> LENGTH: 20
<212> TYPE: DNA
<213> ORGANISM: Homo sapiens

<400> SEQUENCE: 74
cactttggga ggaactcgaa 20

<210> SEQ ID NO 75
<211> LENGTH: 20
<212> TYPE: DNA
<213> ORGANISM: Homo sapiens

<400> SEQUENCE: 75
gtaggggctg tccgtatcaa 20

<210> SEQ ID NO 76
<211> LENGTH: 20
<212> TYPE: DNA
<213> ORGANISM: Homo sapiens

<400> SEQUENCE: 76
atttccccac agctcttcct 20

<210> SEQ ID NO 77
<211> LENGTH: 19
<212> TYPE: DNA
<213> ORGANISM: Homo sapiens

<400> SEQUENCE: 77
acagatgctg ccctctgtg 19

-continued

<210> SEQ ID NO 78
<211> LENGTH: 20
<212> TYPE: DNA
<213> ORGANISM: Homo sapiens

<400> SEQUENCE: 78
aagcccagga ctctcctcat 20

<210> SEQ ID NO 79
<211> LENGTH: 20
<212> TYPE: DNA
<213> ORGANISM: Homo sapiens

<400> SEQUENCE: 79
agtgaaacag ccagtgcaaa 20

<210> SEQ ID NO 80
<211> LENGTH: 20
<212> TYPE: DNA
<213> ORGANISM: Homo sapiens

<400> SEQUENCE: 80
ctggttgctc tgctctaccc 20

<210> SEQ ID NO 81
<211> LENGTH: 20
<212> TYPE: DNA
<213> ORGANISM: Homo sapiens

<400> SEQUENCE: 81
gtatggtgca ctggggattc 20

<210> SEQ ID NO 82
<211> LENGTH: 20
<212> TYPE: DNA
<213> ORGANISM: Homo sapiens

<400> SEQUENCE: 82
ccccttccta tgcctcaaag 20

<210> SEQ ID NO 83
<211> LENGTH: 20
<212> TYPE: DNA
<213> ORGANISM: Homo sapiens

<400> SEQUENCE: 83
taggtgaaaa tgccccaaaa 20

<210> SEQ ID NO 84
<211> LENGTH: 20
<212> TYPE: DNA
<213> ORGANISM: Homo sapiens

<400> SEQUENCE: 84
catttcgctg aagcttgtgt 20

<210> SEQ ID NO 85
<211> LENGTH: 20
<212> TYPE: DNA
<213> ORGANISM: Homo sapiens

<400> SEQUENCE: 85
ccatgcaatg attgttttgc 20

-continued

```
<210> SEQ ID NO 86
<211> LENGTH: 25
<212> TYPE: DNA
<213> ORGANISM: Homo sapiens

<400> SEQUENCE: 86

caaatgtgta tgtttgtatg gtggt                                        25


<210> SEQ ID NO 87
<211> LENGTH: 23
<212> TYPE: DNA
<213> ORGANISM: Homo sapiens

<400> SEQUENCE: 87

tcctttttgt aatgggaagt gaa                                          23


<210> SEQ ID NO 88
<211> LENGTH: 20
<212> TYPE: DNA
<213> ORGANISM: Homo sapiens

<400> SEQUENCE: 88

tacgtgtagc cccacctaag                                              20


<210> SEQ ID NO 89
<211> LENGTH: 20
<212> TYPE: DNA
<213> ORGANISM: Homo sapiens

<400> SEQUENCE: 89

tgtcctcaaa acccacacaa                                              20


<210> SEQ ID NO 90
<211> LENGTH: 20
<212> TYPE: DNA
<213> ORGANISM: Homo sapiens

<400> SEQUENCE: 90

agagcgcgtg tgagactgta                                              20


<210> SEQ ID NO 91
<211> LENGTH: 20
<212> TYPE: DNA
<213> ORGANISM: Homo sapiens

<400> SEQUENCE: 91

agaatttgct gcctgcttgt                                              20


<210> SEQ ID NO 92
<211> LENGTH: 20
<212> TYPE: DNA
<213> ORGANISM: Homo sapiens

<400> SEQUENCE: 92

gctggggagg taaagtgaaa                                              20
```

LONG NON-CODING RNA GENE EXPRESSION SIGNATURES IN DISEASE MONITORING AND TREATMENT

RELATED APPLICATION

The present application claims the benefit of and priority to U.S. provisional patent application Ser. No. 62/568,737, filed Oct. 5, 2017, the contents of which are incorporated by reference herein in their entirety.

TECHNICAL FIELD

The disclosure relates to monitoring disease and therapeutic efficacy using differential expression of long non-coding or enhancer RNA.

BACKGROUND

While the understanding of disease has expanded greatly in recent decades, there are still many serious diseases that the medical community is ill-equipped to diagnose and treat. Many of those diseases exhibit improved outcomes if detected and treated early. Due to a reliance on subjective analysis and diagnoses of exclusion (diagnosing by process of elimination) many patients receive late diagnoses of diseases such as multiple sclerosis (MS) and can suffer shortened life expectancies and a lower quality of life as a result. Because diseases like MS are degenerative and loss of function is cumulative, early detection and treatment can afford significant benefits in delaying further degenerative changes and attacks while patients who begin treatment later do not reap the same benefits as those who begin treatment earlier during the disease course.

Furthermore, with diseases such as MS that are characterized by unpredictable cycles of relapse and remission, it can be difficult to monitor progression of the disease or the therapeutic efficacy of treatments, especially during periods of remission.

For MS, diagnosis currently relies on clinical symptoms and examinations as outlined in the revised McDonald criteria supported by magnetic resonance imaging analysis or other laboratory tests on cerebrospinal fluid or evoked potential testing. Tracking disease progression for MS similarly relies on expensive imaging techniques (e.g., MRI) and functional tests that rely on monitoring symptoms and effects of the disease as opposed to the progression of the underlying disease itself. The lack of accurate and objective techniques for tracking disease progression also impairs the ability to test therapeutic efficacy of new and existing treatments, especially during remission stages of diseases like MS.

SUMMARY

The present invention provides methods for monitoring disease progression and therapeutic efficacy through the analysis of differentially expressed non-coding RNA including long non-coding RNA (lncRNA) or enhancer RNA (eRNA) species. lncRNA are regulatory RNA molecules that are not believed to code for proteins but that influence a vast array of biological processes. They are generally longer than about 200 nucleotides. eRNA are a class of non-coding RNA between about 50 and about 2000 nucleotides in length that are transcribed from enhancer regions of DNA. The present invention recognizes that certain lncRNAs and eRNAs are differentially expressed in various diseases and can therefore be used as disease signatures to track disease progression or to determine therapeutic efficacy through relatively inexpensive, quick, and simple assays on, for example, patient blood samples taken over time. By measuring expression levels of these non-coding RNAs in patients, for example during treatment with a specific therapy, the effectiveness of the treatment can be determined without the need to rely on manifestation of observable symptoms. Such methods are particularly useful in testing therapeutics and monitoring progression of diseases with remission and relapse cycles like MS. In fact, methods of the invention may be useful in predicting relapse in such diseases. Methods and kits of the present invention provide a reliable, non-invasive, and inexpensive tool for monitoring diseases. Furthermore, due to the non-invasive and inexpensive nature of the described methods, subject diseases may be monitored at relatively short intervals, providing greater insight into disease progression and allowing for more rapid response to looming relapses or downturns.

Additionally for broad disease categories generally diagnosed by exclusion, effective treatment may depend on accurate diagnosis of a specific disease subtype as a treatment may have different results depending on the subtype of the disease. Methods of the invention may be used to more accurately differentiate between disease subtypes and even allow for treatment determinations by matching patterns of differential expression of non-coding RNAs to specific treatment outcomes in patient data and then using that information to determine the best treatment in new patients.

Additional factors may be included in disease analysis including medical history and social factors such as demographic information, environmental considerations, patient or family history of disease, smoking, drug use, exercise, socio-economic information, and patient height, weight, or body mass index. Any of the above additional factors may be combined with information regarding expression levels of various non-coding RNAs to diagnose or monitor disease states. By combining data related to the above additional factors with known outcomes for patients, patterns may be identified through, for example, machine learning analysis, to link combinations of the above additional factors and expression levels of non-coding RNAs to various outcomes such that subsequent identification of those patterns in new patients may be indicative of the linked outcome for the new patient.

Other factors that may be included in training sets and subsequent diagnostic and prognostic models may include patient DNA analysis of epigenetic factors and imaging analysis such as histological analysis of patient body fluid or tissue samples.

Methods of the invention are used to monitor, for example, neurological diseases, inflammatory diseases, rheumatic diseases, and autoimmune diseases. Specific diseases that may be monitored using methods of the invention include, for example, multiple sclerosis (MS), Parkinson's disease, Alzheimer's disease, epilepsy, Crohn's disease, ulcerative colitis, IBD (inflammatory bowel disease), systemic lupus erythmatosus, rheumatoid arthritis, and fibromyalgia. In certain embodiments, methods of the invention are used to monitor various types of cancer. In other embodiments, methods may be used to monitor any non-cancer disease. In certain embodiments, systems and methods may be used to diagnose or monitor forms of cancer, infections, genetic disorders, traumatic brain injury, chronic traumatic encephalopathy, heart disease, diabetes, or endocrine disorders.

Analytical devices, such as biosensors may be used to collect, monitor and convey physiological data using the systems and methods described herein. In some embodiments of the invention, analytical devices may be used for conveying diagnostic or prognostic information determined using the systems and methods described herein. In certain embodiments, methods such as color coded reporting may be used for conveying diagnostic or prognostic information determined using the analytical systems and methods described herein. Physiological, diagnostic and prognostic information collected by the analytical device may be integrated with lncRNA or eRNA expression data to monitor or track identified patterns or signals over time and provide alerts when various thresholds are passed.

Methods of the invention are used to anticipate the onset of certain symptoms (e.g., a relapse in MS). Methods of the invention may be used to determine disease progression or grade. In certain embodiments, methods of the invention relate to identifying lncRNAs or patterns of lncRNAs that exhibit differential expression in patients that respond well to a certain type of treatment. For example, machine learning analysis of lncRNA or eRNA expression data in patient cohorts with known treatment histories may be used to train systems for determining the best course of treatment for a given patient.

Aspects of the invention may include methods of monitoring disease progression in a subject. Steps of the method may include isolating ribonucleic acid (RNA) from a first sample and a second sample from a patient wherein the second sample is collected from the patient at a later point in time than the first sample. An assay may be conducted on the RNA from the first and second samples to measure expression levels of a long non-coding RNA (lncRNA) species. The expression levels can be compared to a reference expression level to determine differential expression of the lncRNA gene in the first and second samples and disease progression can be determined based on an increase or decrease in differential expression between the lncRNA gene in the first and second samples.

A decrease in differential expression between the first and second samples may be indicative of a lower disease burden. The patient may receive a treatment for the disease in between collection of the first and second samples, and the method can further comprise determining a therapeutic efficacy of the treatment based on the determined disease progression. The disease may be a neurological disease, an inflammatory disease, a rheumatic disease, or an autoimmune disease.

Methods may include measuring expression levels of a plurality of lncRNA species in the first and second samples and determining presence of disease where the expression levels are different than reference expression levels. The disease may be multiple sclerosis (MS).

Disease monitored using methods and kits of the invention include, for example, Parkinson's disease, Alzheimer's disease, or epilepsy. The disease can be Crohn's disease, ulcerative colitis, or 1BD (inflammatory bowel disease). The disease may be systemic lupus erythmatosus, rheumatoid arthritis, or fibromyalgia.

The first and/or second sample may be blood, saliva, sputum, urine, semen, transvaginal fluid, cerebrospinal fluid, sweat, stool, a cell or a tissue biopsy. The assay may include a reverse transcription polymerase chain reaction (RT-PCR).

Methods may include conducting an assay on the RNA from the first and second samples to measure an expression level of a housekeeping gene and normalizing the expression level of the lncRNA gene to the expression level of the housekeeping gene. The housekeeping gene can be GAPDH, ACTB, B2M, 18S, or 28S.

Aspects of the inventing may include methods of identifying treatment indicator biomarkers. For example, expression levels of lncRNA from samples obtained from patients known to have a particular response to a specific therapy are curated and introduced to a machine learning algorithm as a training set. Unknown samples are then applied to the algorithm for therapy determination. The training algorithm may be a standard machine learning algorithm or may be a custom design. In any case, the algorithm learns to associate differential expression of lncRNA and/or eRNA or a combination thereof) with responsiveness to certain therapies. When an unknown sample is presented, the algorithm determines the likely response of the patient to one or more therapies. That may be done by a simple matching algorithm or other means as determined by the programmer.

The machine learning system can be selected from the group consisting of a random forest, a support vector machine (SVM), and a boosting algorithm. Methods may include calculating ratios between each pair of expression levels of the plurality of lncRNA species and providing the ratios to the machine learning system. The known disease outcomes may include at least three distinct outcomes and wherein the plurality of differentially expressed lncRNA species is determined using a plurality of machine learning systems for each pair of the at least three distinct outcomes and the method may include providing outputs from each of the plurality of machine learning systems to train a multi-category classifier for differentiating between the at least three distinct outcomes based on lncRNA expression levels. In certain embodiments, the plurality of lncRNA species comprises an enhancer RNA (eRNA).

In certain aspects, methods of the invention may include determining treatment for a subject by: isolating ribonucleic acid (RNA) from a patient sample, wherein the patient has been diagnosed with a disease; conducting an assay on the RNA to measure an expression level of a non-coding RNA species; and determining a recommended treatment for the disease where the expression level is different than a reference expression level. The non-coding RNA may be a long non-coding RNA (lncRNA). The non-coding RNA can be an enhancer RNA (eRNA).

Aspects of the invention can include a kit comprising primer pairs for determining expression levels of one or more lncRNA species found to be differentially expressed in individuals having a disease. In certain embodiments, the disease may be MS. In certain embodiments, the diseases may be FMS, RA, and SLE and the primers may be selected from SEQ ID NOs: 1-92.

In certain aspects, methods of the invention may include methods for monitoring the status of a disease or disease burden in a subject. Steps of the methods can include isolating ribonucleic acid (RNA) from a patient sample, conducting an assay on the RNA to measure an expression level of a enhancer RNA (eRNA) gene, and determining disease burden based on the relative increase or decrease of differential expression levels in samples taken from a patient over time. In certain embodiments the disease is selected from the group consisting of a neurological disease, an inflammatory disease, a rheumatic disease, and an autoimmune disease.

BRIEF DESCRIPTION OF THE DRAWINGS

FIG. 10 shows an exemplary vector of binary classifier output used to train hybrid-classifier or multi-category classifier.

FIG. 11 compares accuracy various machine learning systems trained as binary classifiers using differentially expressed mRNAs and lncRNAs.

FIG. 16 depicts ROC curves of mRNA and lncRNA datasets versus a control.

FIG. 18 shows a summary of accuracy, sensitivity, and specificity of MS, OND-I, or OND-NI multi-category classifiers.

DETAILED DESCRIPTION

Figure 1:
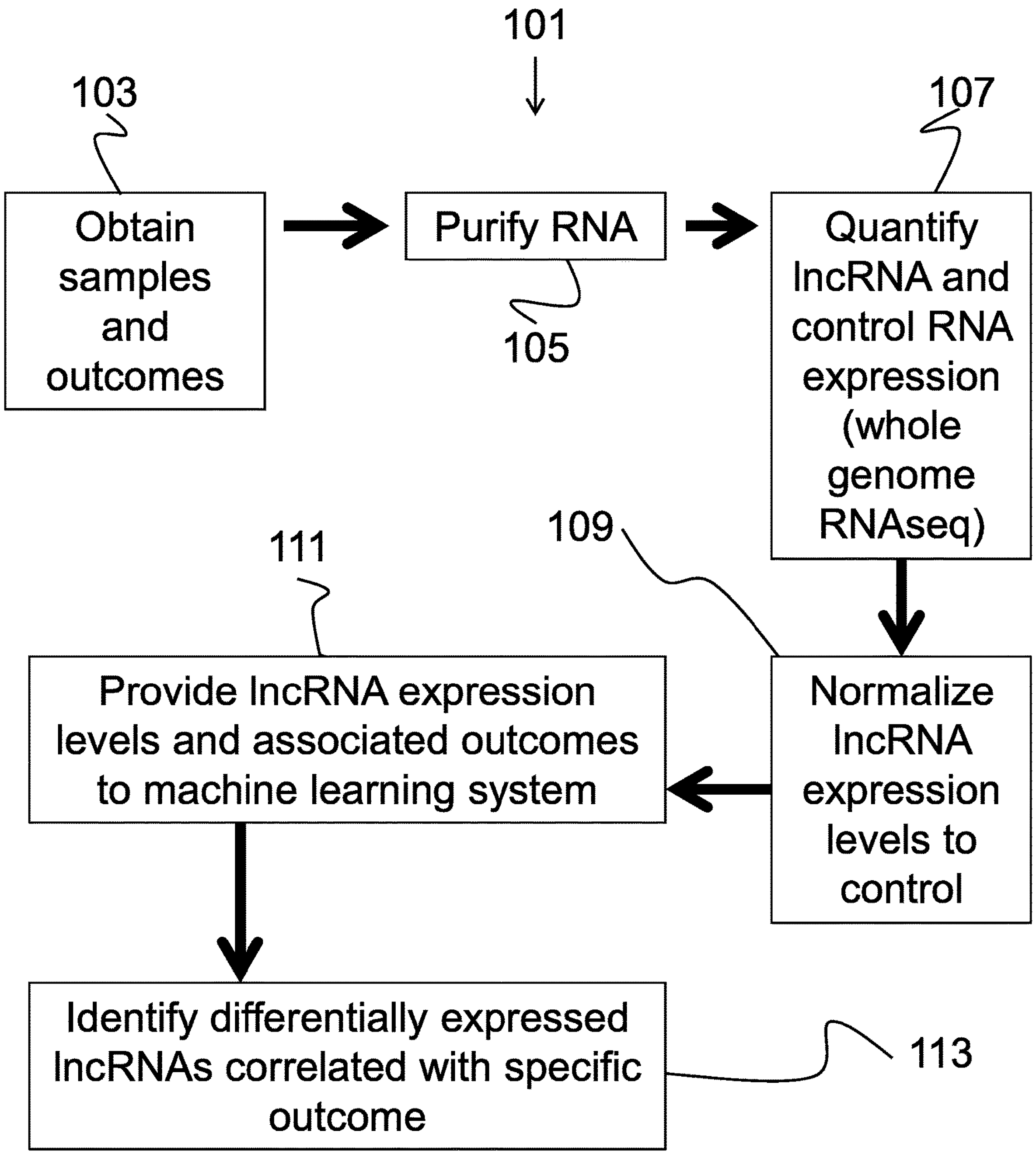
FIG. 1 diagrams steps of a machine learning method for identifying lncRNAs differentially expressed in populations with a given response to a specific therapy.

Methods and kits of the invention relate to monitoring disease progression or therapeutic efficacy based on differential expression of one or more lncRNAs or eRNAs in a patient sample or a series of patient samples taken over time. Measuring differential expression of various lncRNAs or eRNAs can provide a cheap and accurate tool for various hard to track neurological diseases, inflammatory diseases, rheumatic diseases, and autoimmune diseases. By providing accurate tracking of the progression of degenerative diseases such as MS, kits and methods of the invention allow for earlier and better intervention and increased understanding of a patient's prognosis. Accordingly, methods and kits of the invention can prolong life expectancies, and increase patients' quality of life. In various embodiments, methods of the invention provide for monitoring of diseases such as multiple sclerosis (MS), Parkinson's disease, Alzheimer's disease, epilepsy, Crohn's disease, ulcerative colitis, IBD (inflammatory bowel disease), systemic lupus erythmatosus, rheumatoid arthritis, and fibromyalgia through analysis of expression levels of one or more lncRNAs or eRNAs and comparison to threshold expression levels. Differential expression of those non-coding RNAs can be tracked over time through periodic sampling of a patient to determine disease progression or monitor response to treatments.

Increased or decreased differential expression of certain RNAs or patterns RNAs can indicate that a patient is improving or getting worse and may be used to predict relapses or other specific events in disease cycles through spikes in differential expression or other observable changes in a patient's non-coding RNA expression profile. The expression levels may be determined through assays such as RT-PCR performed on RNA obtained from patient samples such as blood. By providing for accurate disease diagnosis from a simple blood draw, methods and kits of the invention constitute a significant advance over existing techniques for diseases such as MS that rely on expensive imaging techniques and general symptom-based grading.

Additional patient information such as family or patient medical histories, smoking, alcohol consumption, drug use, socio-economic, demographic, or physical characteristics (e.g., height, weight, BMI) may be incorporated, along with expression levels, into machine learning analyses and subsequent diagnostic and prognostic testing and monitoring.

Furthermore, standard diagnostic techniques including magnetic resonance imaging analysis, biopsy and histological analysis, patient functional tests, and any other patient-specific information may be included in training sets and subsequent disease monitoring or diagnostic models. The more data that is included in initial analyses, the more likely an algorithm will be able to identify pattern that accurately and sensitively predicts patient outcome.

In certain embodiments, conventional DNA analysis of patient samples may be conducted in concert with non-coding RNA analysis. Known disease-linked epigenetic factors such as methylation patterns and histone modifications may be combined with non-coding RNA patterns to diagnose or monitor diseases. Such information may be included along with non-coding RNA expression data and known patient outcomes in training sets in order to identify new disease-indicative patterns or may be incorporated in subsequent application of diagnostic models developed using machine learning techniques as described herein. For example, the presence of a DNA mutation with known links to a certain disease may be used to confirm or bolster a prognostic determination made using non-coding RNA expression analysis. Such DNA data may be useful in cases where RNA information is incomplete due to the relative instability of RNA compared to DNA, especially cell-free RNA as opposed to RNA harvested from freshly lysed cells.

Supplemental DNA analysis may include mutational screening via targeted amplification or immunoassay, sequencing, or epigenetic factor screening. Supplemental DNA information may include, for example, single-nucleotide polymorphisms, methylation, histone modifications, deletions, substitutions, copy-number variation, microsatellite instability, or chromosomal mutations. As noted below non-coding RNA is obtained, preferably as cell-free RNA, from body fluid samples. Accordingly, DNA such as cell-free DNA can be obtained from the same samples for analysis, avoiding the need for additional blood draws or other sampling.

Because of the reduced costs and the non-invasive nature of the claimed techniques, methods of the invention may be applied at frequent intervals to allow for earlier detection of disease developments or milestones and, where said developments require specific treatment, faster treatment thereof. In certain embodiments, the invention provides kits comprising primer pairs for determining expression levels of lncRNAs or eRNAs associated with various diseases and therefore useful in monitoring disease progression, determining therapeutic efficacy, or determining the best course of treatment for specific subject and disease.

In various embodiments, methods of the invention relate to identifying lncRNAs or eRNAs that are differentially expressed in disease-positive patients that exhibit a certain response to a specific treatment. Machine-learning analysis of expression levels and treatment outcomes for specific therapies may be used for that purpose.

Long non-coding RNAs (lncRNAs) are regulatory RNA molecules that do not code for proteins but influence a vast array of biological processes. See Spurlock, et al., 2016, Biogenesis and transcriptional regulation of long non-coding RNAs in the human immune system, Journal of Immunology, 197:4509-4517, incorporated herein by reference. The lncRNA designation is generally restricted to non-coding transcripts longer than about 200 nucleotides. The length designation differentiates lncRNA from small regulatory RNAs such as short interfering RNA (siRNA) and micro RNA (miRNA). In vertebrates, the number of lncRNA species is thought to greatly exceed the number of protein-coding species. It is also thought that lncRNAs drive biologic complexity observed in vertebrates compared to invertebrates. Evidence of this complexity is seen in many cellular compartments of a vertebrate organism such as the T lymphocyte compartment of the adaptive immune system. Without wishing to be tied to a particular theory, it is believed that differences in expression and function of lncRNAs are major contributors to complex human disease. Methods of the invention recognize that lncRNA expression may be associated with certain diseases and exhibit far greater differences in expression than disease-associated mRNAs. Accordingly, lncRNAs, which may have been overlooked by researchers because they do not code for proteins, can in fact provide keen insights into disease through comparative measurements of their expression in patients.

eRNAs are non-coding RNA molecules between 50-2000 nucleotides that are transcribed from enhancer regions of DNA. eRNA expression has been found to correspond to the activity of its enhancer. eRNAs have been implicated in transcriptional regulation. eRNA and lncRNA classifications can overlap in instances of eRNA longer than about 200 nucleotides. Like lncRNAs, eRNA has not traditionally been treated as a biomarker for disease, probably due to its non-coding status however, the present invention recognizes that certain eRNAs, a with lncRNAs, can exhibit distinct expression signatures based on certain disease states. Methods and kits of the invention rely on these signatures to diagnose and treat otherwise difficult to detect diseases. Methods and kits described herein may be equally applied to identify differentially expressed, disease associated lncRNAs and eRNAs. Descriptions herein that refer only to either lncRNA or eRNA alone should be understood to be equally applicable to either.

In certain embodiments, methods of the invention may be used to determine unique lncRNA or eRNA signatures associated with positive responses to specific therapies in disease populations. Expression levels for known and unknown lncRNA or eRNA sequences may be determined using, for example, RNA-Seq or whole transcriptome shotgun sequencing for a series of samples from patients having a certain disease and a known response to a specific treatment (e.g., a patients with MS that exhibited good response to beta interferons or another treatment).

For example, known whole genome sequencing techniques such as TruSeq whole-transcriptome analysis from Illumina, Inc., (San Diego, California) may be used. RNA can be selected based on size during library preparation (e.g., targeting RNA longer than 200 nucleotides) using techniques such as size exclusion gel or size selection magnetic beads. Analysis tools such as TopHat2 (Johns Hopkins University for Computational Biology), Cufflinks (University of Washington, Cole Trapnell Lab), and DESeq2 (See Love M I, Huber W and Anders S, 2014, Moderated estimation of fold change and dispersion for RNA-seq data with DESeq2, Genome Biology, 15, pp. 550, incorporated herein by reference) may be used to align RNA sequences and to determine expression levels and identify differential expression of lncRNA or eRNA. RNA may be obtained from patient biological samples such as blood, saliva, sputum, urine, semen, transvaginal fluid, cerebrospinal fluid, sweat, breast milk, nipple aspirate, stool, a cell or a tissue biopsy. RNA may be isolated from cells through lysis thereof or may be obtained as cell-free RNA observed in biological samples such as body fluids obtained from a patient.

In preferred embodiments, samples may be peripheral whole blood. Blood can be collected from subjects having known disease status or from test subjects and may be analyzed immediately or stored in, for example, PAXgene Blood RNA tubes available from Qiagen N.V. (Hilden, Germany) or other RNA stabilizing storage mechanisms. RNA may be isolated and purified or cleaned using commercially available kits such as the PAXgene RNA kit available from Qiagen N.V. (Hilden, Germany).

By comparing expression levels of lncRNAs and eRNAs in patients that exhibited positive response to various treatments one can identify lncRNAs or eRNAs that are differentially expressed in each of the various treatments. Accordingly, differential expression of those lncRNAs or eRNAs may be measured in patients having a disease to determine likely response to the various treatments and to thereby determine the best course of treatment. In certain embodiments, the lncRNA and/or eRNA expression data and associated known treatment outcomes may be subjected to machine learning analysis to identify patterns of differential expression most predictive of therapeutic response. lncRNA or eRNA levels may by normalized against measured expression levels of a housekeeping gene from the same sample. Suitable housekeeping genes may include GAPDH, ACTB, B2M, 18S, and 28S.

FIG. 1 shows steps of an exemplary method 101 for identifying lncRNAs associated with therapy outcomes using machine learning systems. In the exemplary method of FIG. 1, samples from patients with known disease states and therapy outcomes for specific treatments are obtained 103 as described above and RNA may be extracted and purified 105 using the techniques mentioned earlier. Differentially expressed lncRNAs are identified from whole genome sequencing data 107. The data may be normalized to expression levels of controls (e.g., housekeeping gene) 109. Differentially expressed lncRNAs are provided to a machine learning system, along with the known disease states and therapy outcomes of the patients from whom the differentially expressed lncRNAs were obtained 111. The machine learning system is used to identify lncRNAs with over or under expression most correlated with specific therapy outcomes 113.

Methods of the invention may include applying a ratio-score analysis to the expression levels. See, Tossberg J T, Crooke P S, Henderson M A, Sriram S, Mrelashvili D, Chitnis S, Polman C, Vosslamber S, Verweij C L, Olsen N J, Aune T M: Gene-expression signatures: biomarkers toward diagnosing multiple sclerosis. Genelmmun 2012, 13:146-154, incorporated herein by reference. Through the application of ratioscore analysis, expression ratios of two species rather than a single gene can be used as inputs for subsequent machine learning systems. By using gene ratios, the data can be normalized independent of any measured housekeeping gene and does not rely on the housekeeping gene being consistently expressed at the same level across samples.

Additionally, by using ratios of over-expressed species to under-expressed species, a greater quantitative difference can be produced than when using a single species. For example, if one gene is consistently over-expressed by two-fold and a second gene is consistently under-expressed by two-fold, then the ratio of the two species would produce a fourfold difference in a case-control comparison. All possible ratios can be calculated and then optimized through, for example, permutation testing to identify the most strongly correlated ratios to the disease. By the above method, the smallest number of ratios representing the maximum separation between a responsive and non-responsive group for a specific therapy can be determined.

Expression levels or, in preferred embodiments, the ratio values determined using ratioscore analysis above, can be input along with their associated therapy outcomes into various machine learning algorithms to identify differentially expressed lncRNAs or eRNAs or patterns or combinations thereof that are most indicative of the outcome being tested for.

Any machine learning algorithm may be used to analyze RNA differential expression levels including, for example, a random forest, a support vector machine (SVM), or a boosting algorithm (e.g., adaptive boosting (AdaBoost), gradient boost method (GSM), or extreme gradient boost methods (XGBoost)), or neural networks such as H2O. Machine learning algorithms generally are of one of the following types: (1) bagging, (2) boosting, or (3) stacking. In bagging, multiple prediction models (generally of the same type) are constructed from subsets of classification data (classes and features) and then combined into a single classifier. Random Forest classifiers are of this type. In boosting, an initial prediction model is iteratively improved by examining prediction errors. Adaboost.M1 and eXtreme Gradient Boosting are of this type. In stacking models, multiple prediction models (generally of different types) are combined to form the final classifier. These methods are called ensemble methods. The fundamental or starting methods in the ensemble methods are often decision trees. Decision trees are non-parametric supervised learning methods that use simple decision rules to infer the classification from the features in the data. They have some advantages in that they are simple to understand and can be visualized as a tree starting at the root (usually a single node) and repeatedly branch to the leaves (multiple nodes) that are associated with the classification.

Random forests use decision tree learning, where a model is built that predicts the value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, L. Random Forests, Machine Learning 45:5-32 (2001), incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable.

SVMs can be used for classification and regression. When used for classification of new data into one of two categories, such as having a disease or not having a disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering. See Ben-Hur, A., et al., (2001), Support Vector Clustering, Journal of Machine Learning Research, 2:125-137.

Boosting algorithms are machine learning ensemble meta-algorithms for reducing bias and variance. Boosting is focused on turning weak learners into strong learners where a weak learner is defined to be a classifier which is only slightly correlated with the true classification while a strong learner is a classifier that is well-correlated with the true classification. Boosting algorithms consist of iteratively learning weak classifiers with respect to a distribution and adding them to a final strong classifier. The added classifiers are typically weighted in based on their accuracy. Boosting algorithms include AdaBoost, gradient boosting, and XGBoost. Freund, Yoav; Schapire, Robert E (1997). "A decision-theoretic generalization of on-line learning and an application to boosting". Journal of Computer and System Sciences. 55: 119; S. A. Solla and T. K. Leen and K. Müller. Advances in Neural Information Processing Systems 12. MIT Press. pp. 512-518; Tianqi Chen and Carlos Guestrin. XGBoost: A Scalable Tree Boosting System. In 22nd SIGKDD Conference on Knowledge Discovery and Data Mining, 2016; the contents of each of which are incorporated herein by reference.

Figure 9:
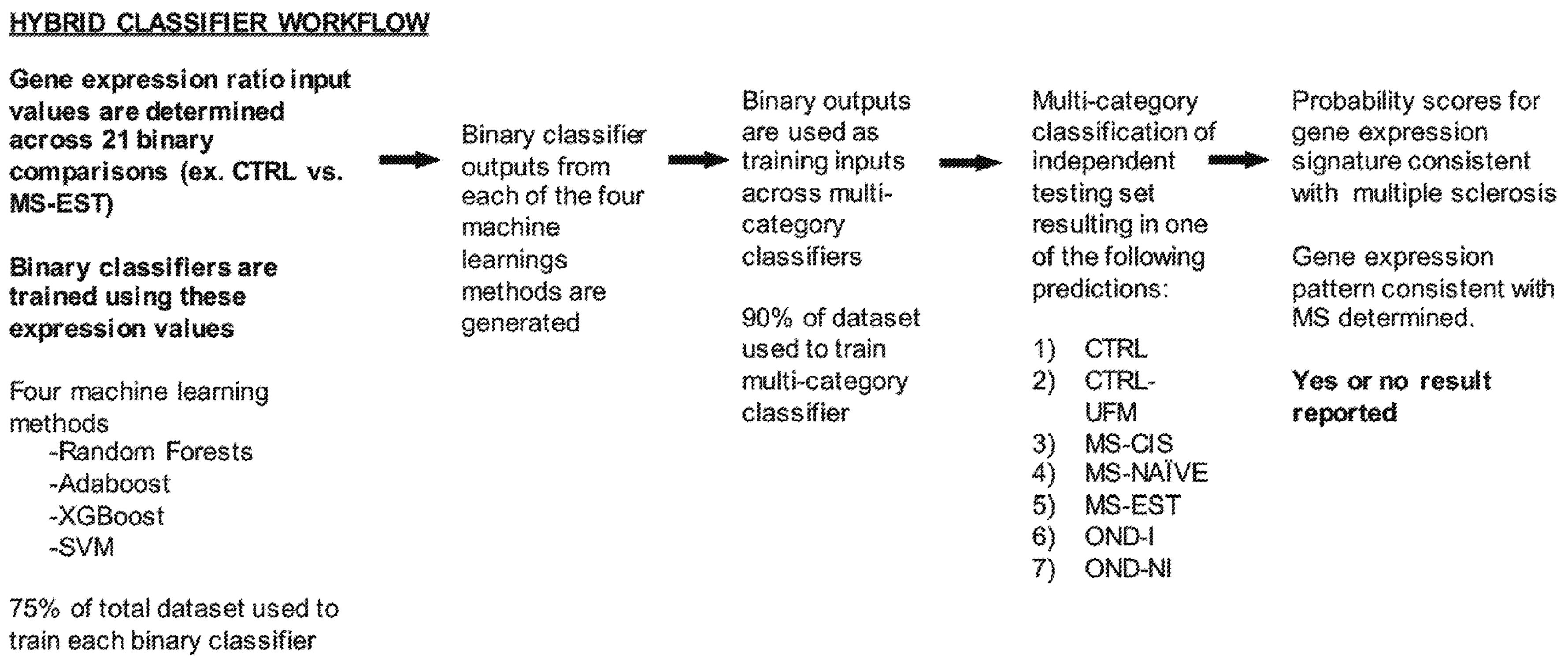
FIG. 9 diagrams a hybrid classification workflow.

In certain embodiments, a hybrid classifier system may be used to distinguish between patients with different responses to a specific therapy as discussed herein. For example, a series of independent binary classifiers can be used to generate outputs that are evaluated in a second set of binary inputs to create a multi-category classification based only on binary comparisons. Accordingly, such methods can be used to overcome some of the shortcomings of machine learning techniques applied to multi-category classification while taking advantage of those machine learning techniques strong binary classifications. FIG. 9 diagrams a hybrid classification workflow. Binary classifiers are trained using measured lncRNA or eRNA expression data from paired categories of patient populations (e.g., any two of: positive response to treatment A, positive response to treatment B, or unresponsive to treatment A or B). Outputs from those binary classifiers are generated using a plurality of machine learning methods (e.g., random forests, AdaBoost, XGBoost, and SVM) and then used as inputs in a multi-category analysis (e.g., classifying among 3 or more categories such as responsive or unresponsive to therapy A, B, C, or D) using one or more machine learning methods as described above. In certain embodiments, hybrid classifiers may be created as follows: Trained binary classifiers capable of discriminating individual subclasses (e.g. therapy outcomes) can be applied to a dataset comprising lncRNA expression levels. For each control and therapy outcome class, the output of the binary classifiers can be used to create a vector for each patient in the dataset. An exemplary vector is shown in FIG. 10. The vectors may then be used to train each multi-category classifier. Different combinations of input binary classifiers and multi-category classifiers can be used.

Methods of the invention include diagnostic tests based on measured lncRNA or eRNA expression levels. After lncRNAs or eRNAs have been identified as being differentially expressed in patients with certain responses to various therapies, their expression levels may be measured in test subjects at diagnosis of disease and used to predict response to a specific therapy. If a lncRNA or eRNA expression level indicates that a patient will respond better to one treatment than another, steps of the method may include, for example, providing that information in a written report, or prescribing and/or administering the better suited of the treatments. In preferred embodiments, lncRNA or eRNA expression level indicates that a patient will respond better to one inflammatory disease treatment than another. In another preferred embodiment, the treatment indicated is a cancer treatment. In certain embodiments, a set of lncRNA or eRNA expression levels may be defined and measured to diagnose a disease and determine a treatment regimen in a single multiplex analysis through methods of kits of the invention.

Methods of the invention also include monitoring response to a treatment based on measured lncRNA or eRNA expression levels over the course of a treatment. Such methods include obtaining a reference sample from the patient before treatment to obtain reference lncRNA or eRNA expression levels. Clinical samples may be obtained from the patient from time to time during the course of treatment and the lncRNA or eRNA expression levels may be measured and compared to the reference sample expression levels. Changes in the expression levels during the course of treatment may be indicative of therapeutic efficacy of the treatment.

Figure 2:
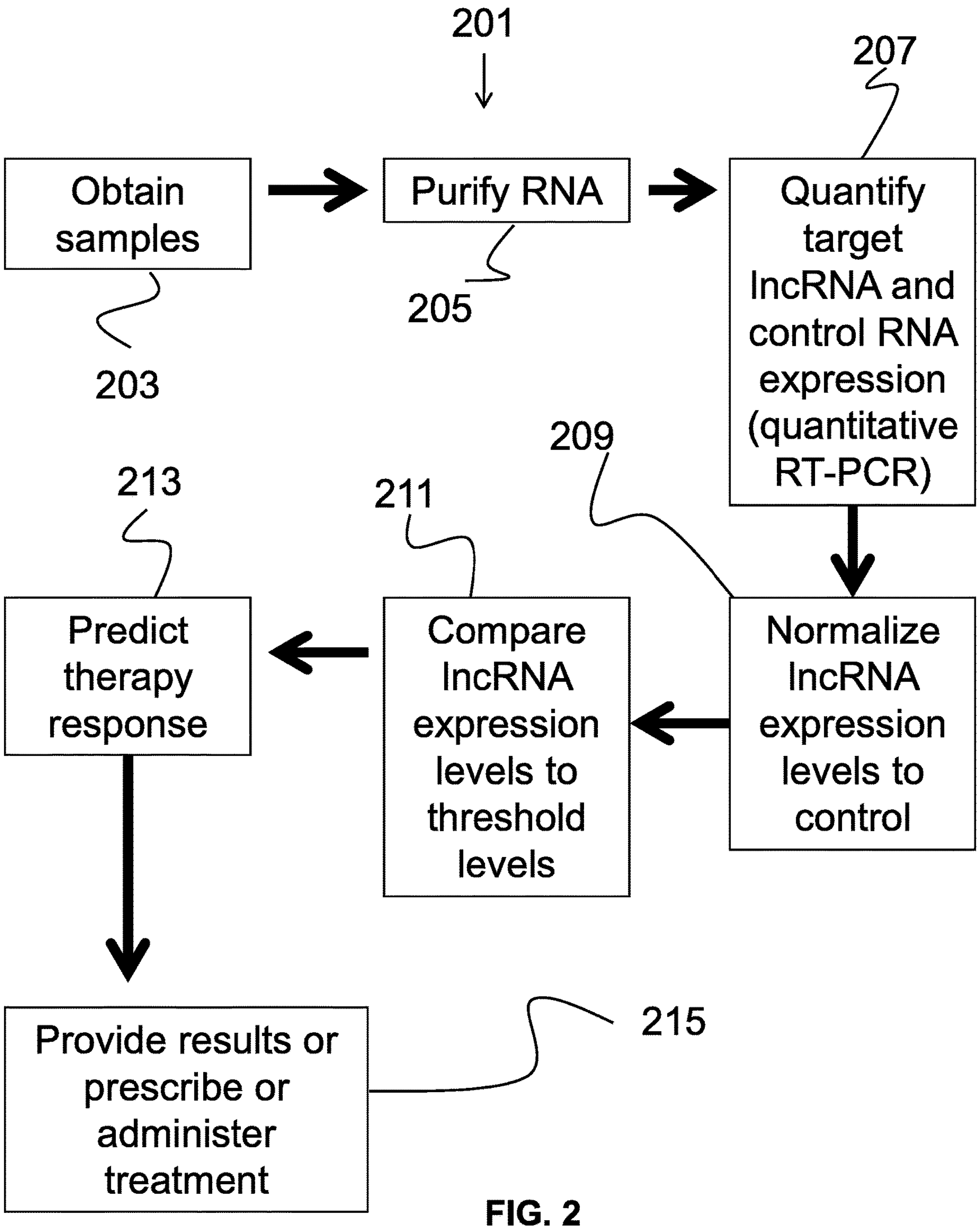
FIG. 2 diagrams steps of an exemplary method for determining treatment for a disease based on differential expression of lncRNAs.

FIG. 2 shows an exemplary method 201 for determining a treatment regimen. In the exemplary method, a sample is obtained from a patient 203. The sample may comprise blood, saliva, sputum, urine, semen, transvaginal fluid, cerebrospinal fluid, sweat, breast milk, nipple aspirate, stool, a cell or a tissue biopsy. RNA can be isolated from the sample using any known technique and may be stored and/or purified 205 as described above. Expression of target lncRNAs and control RNAs (e.g., housekeeping gene) are then quantified 207. Quantification may be accomplished through quantitative RT-PCR using primers designed to amplify lncRNAs that are over or under expressed in certain disease states. Expression data may be normalized 209 to expression levels of a housekeeping gene or other control measured in the sample. In certain embodiments, pairs of lncRNAs or eRNAs may be analyzed to determine expression ratios that may be predictive of a response to one or more therapies. The normalized expression levels may be compared 211 to a threshold level for each respective lncRNA and, based on over or under expression of one or more lncRNAs compared to their respective thresholds, a therapeutic response may be predicted 213 for one or more treatment methods that corresponds to that pattern of differential expression. Threshold expression levels may be determined, for example, by measuring average expression of the lncRNA or eRNA in a cell line (e.g., Jurkat cells or other human cell lines). In certain embodiments, thresholds may be determined from expression levels in healthy relatives of the patient or may be compared to expression levels in earlier samples from the patient. A probable response to a specific therapy may thereby be predicted for the patient and the patient may be provided with the predicted response, or prescribed or administered treatment if a positive response is indicated 215.

For example, where the disease is an autoimmune disease, response may be predicted for immunosuppressant drugs or anti-TNFmedications. Where the disease is MS, response may be predicted for ocrelizumab, beta interferons, glatiramer acetate, dimethyl fumarate, fingolimod, teriflunomide, natalizumab, alemtuzumab, or mitoxantrone. Where the disease is RA, response may be predicted for physical therapy, anti-inflammatories, steroids, or immunosuppressive drugs. Where the disease is FMS, response may be predicted for pain medication, nerve blocking, muscle relaxants, or a selective serotonin reuptake inhibitor (SSRI). Where the disease is SLE, response may be predicted for steroids or immunosuppressive therapies. Where the disease is cancer, response may be predicted for chemotherapy, immunotherapy, or hormone therapy, or radiation.

In certain embodiments, analytical devices, such as biosensors, may be used to collect, monitor and convey physiological data using the systems and methods described herein. Suitable biosensors include, for example, electrochemical, thermometric, heartrate, optical, piezoelectric, gravimetric, blood glucose, or pyroelectric biosensors that may be used at home or in a clinic. In other embodiments, biosensors may be wearable. Suitable wearable biosensors include, for example, wearable biosensors in a smartwatch, such as the smartwatch sold under the trademark APPLE WATCH, or wearable biosensors in an activity tracker, such as the activity tracker sold under the trademark FITBIT. In embodiments of the invention, analytical devices may be used for conveying diagnostic or prognostic information determined using the systems and methods described herein.

In certain embodiments, methods such as color coded reporting may be used for conveying diagnostic or prognostic information determined using the analytical systems and methods described herein. Analytical devices may be used for conveying the color coded reporting described herein. In order to simplify diagnostic information, specific codes that are indicative of suggested action may be used. For example, a blue color may be used to indicate a low level of risk wherein no action need be taken. A green color may indicate a slightly increased level of risk wherein medical intervention, such as additional testing, should be sought at the patient's convenience. Such an indication may trigger more expensive and/or invasive traditional diagnostic analysis such as a biopsy for example. A red color may be used to indicate a high level of risk or an emergency in which the patient should seek immediate medical attention. The above colors are provided as exemplary indicators and the number and style of the indicator codes may change as one of skill in the art would see fit. For a more nuanced system for example, 5, 10, 15, or more separate indicator codes may be used. Colors, shapes, numbers, letters, or other symbols can be used to convey diagnostic information and recommended action.

Diagnostic and prognostic information such as the aforementioned codes may be provided via a care management system used to monitor or track identified patterns or signals (e.g., non-coding RNA expression levels, epigenetic DNA factors, conventional diagnostic imaging, or social data)

over time and provide alerts when various thresholds are passed. Analytical devices, such as the biosensors described herein may be used to collect physiological, diagnostic and prognostic information, which may be integrated with lncRNA or eRNA expression data to monitor or track identified patterns or signals over time and provide alerts when various thresholds are passed. The information may be transmitted to the care management system. Alerts may be provided to the patient via the analytical device and to the clinic via the care management system. In certain embodiments, the monitoring may include monitoring adherence to treatment protocols and the alerts may include reminders to comply with treatment. In other embodiments, the monitoring may include treatment efficacy.

Kits and methods of the invention may be directed at monitoring progression or severity of a disease in a subject. Diseases contemplated by the invention include, for example neurological diseases, inflammatory diseases, rheumatic diseases, and autoimmune diseases. In certain embodiments, diseases may be any non-cancer disease. In certain embodiments, systems and methods may be used to diagnose or monitor forms of cancer, infections, genetic disorders, traumatic brain injury, chronic traumatic encephalopathy, heart disease, diabetes, or endocrine disorders. Diseases may be inflammatory neurological diseases (e.g., acute disseminated encephalomyelitis, Bell's palsy, CNS lupus, Guillaine Barre, myasthenia gravis, neuromyelitis optica, optic neuritis, and transverse myelitis) or non-inflammatory neurological diseases (e.g., Alzheimer's, cerebral ataxia, cerebral bleed, cervical radiculopathy, drug-induced movement disorder, dystonia, epilepsy, essential tremor, Huntington's disease, hydrocephalus, median neuropathy, meningioma, migraine, Parkinson's disease, pseudotumor, restless leg syndrome, seizures, spasmodic torticollis, stroke, Tourette's syndrome, and transient ischemia). In certain embodiments, diseases may include all non-cancer diseases. In other embodiments, diseases may include cancers.

In certain embodiments, methods may include measuring expression levels of one or more lncRNA or eRNA species and determining a severity of disease based on differential expression levels thereof (e.g., where the lncRNA or eRNA species are over or under expressed relative to, for example, a threshold level). In certain embodiments, the degree of over or under expression is indicative of the severity of disease. In other embodiments, the number and pattern of differentially expressed lncRNA or eRNA species may indicate disease severity or state.

In certain embodiments, expression of one or more specific lncRNA or eRNA species may be measured in a panel over a period of time to monitor disease progression. For example, samples (as described above) may be obtained from a patient at various intervals (e.g., daily, weekly, monthly, or yearly) and changes in differential expression of disease-associated lncRNAs or eRNAs may be measured in the various samples to determine a patient's disease burden: if the patient is getting worse or better, if a specific treatment is working, or to predict remission, a relapse, downturn, flare-up, attack, or episode in diseases such as MS. As discussed in example 1 below and shown in FIG. 3, differential expression of various lncRNAs can be used to differentiate not only between healthy and disease populations but to differentiate between various sub-populations within the broader disease population.

As noted above, methods and kits of the invention may be used to determine therapeutic efficacy of a treatment. Expression of disease-linked non-coding RNAs, such as certain lncRNAs and eRNAs, may be monitoring in patient samples taken during the course of a treatment and changes in the differential expression of those RNAs may indicate that a treatment is working or not and/or the degree to which the patient is responding to the treatment. In certain embodiments, differential expression of non-coding RNAs may be monitored in a patient receiving a clinically accepted treatment in order to determine that specific patient's responsiveness to the treatment and to inform future treatment decisions. For example, where the initial treatment is not having the anticipated effect (e.g., decreasing differential expression of the measured non-coding RNAs), methods of the invention may include determining an alternative treatment or even prescribing or administering an alternate treatment or supplementing the initial treatment. In some embodiments, methods and kits of the invention may be used for experimental therapies or in drug discovery or clinical trials to determine the effectiveness of new previously uncharacterized treatments. In both instances, samples (e.g., blood samples) may be taken at various intervals (e.g., regular time intervals or event-based intervals) during a patient's treatment with the therapy and changes in the differential expression of specific non-coding RNAs associated with the patient's disease will show effectiveness of the treatment.

As an example, kits for diagnosing FMS may include primers designed to amplify one or more of the above lncRNA species. Exemplary primers may comprise the sequences listed below in Table 1. In certain embodiments, primers may share about 90% sequence identity with the primers listed in Table 1.

Kits for diagnosing rheumatoid arthritis may include primers designed to amplify one or more of the above lncRNA species. Exemplary primers may comprise the sequences listed below in Table 2. In certain embodiments, primers may share about 90% sequence identity with the primers listed in Table 2.

Kits for diagnosing Systemic Lupus Erythromatosis may include primers designed to amplify one or more of the above lncRNA species. Exemplary primers may comprise the sequences listed below in Table 3. In certain embodiments, primers may share about 90% sequence identity with the primers listed in Table 3.

In various embodiments, the disease may be Parkinson's disease, Alzheimer's disease, epilepsy, Crohn's disease, ulcerative colitis, IBD (inflammatory bowel disease), systemic lupus erythmatosus, rheumatoid arthritis, or fibromyalgia.

In certain embodiments, kits of the invention include a plurality of primers designed to amplify lncRNAs that are differentially expressed in specific disease states. Kits may be directed at a specific disease such as MS, FMS, RA, or SLE or other inflammatory or non-inflammatory neurological diseases. In certain embodiments, stages or severity of a disease may be marked by differential expression of different non-coding RNAs or patterns of non-coding RNAs, For example, differential expression of lncRNAs A and B may indicate an early, low-grade stage of a certain disease while differential expression of eRNAs C and D may indicate an advanced stage of the same disease. In such instances, methods and kits of the invention may be used to monitor expression of both sets of non-coding RNAs (e.g., use primers for lncRNAs A and B and eRNAs C and D on each sample obtained from the patient) to determine disease burden or therapeutic efficacy.

EXAMPLES

Example 1

Peripheral whole blood was collected into PAXgene tubes from healthy control subjects (N=8), and MS patients at three different stages in the diagnostic process (1) patients with a clinically isolated syndrome (8) who later developed multiple sclerosis (CIS→MS; n=6), (2) MS patients at the time of diagnosis prior to the initiation of therapies (MS-naïve; n=6), and (15) MS patients greater than or equal to 1 year after diagnosis receiving different therapies (MS-established; n=6). Total RNA from PAXgene tubes was used to prepare sequencing libraries using the Illumina Tru-Seq RNA kit with oligo-dT as the primer. 100 bp paired-end reads were generated with an Illumina Hi-Seq 2500. A quality control step was initially performed using tools such as Fastx Toolkit and FastQC (30-34). The RNA data were aligned with TopHat2 and gene expression levels were quantified using Cufflinks and are reported as FPKM (fragments per kilobase per million reads). Differentially expressed species were determined using DESeq2. False discovery rate (FDR<0.05) was used for multiple test correction. GTF files for messenger RNAs and long non-coding RNAs were obtained from GENCODE (release 19; GRCh37.p13). A 0.5 FPKM cutoff was used for lncRNAs and mRNAs across these sequencing data.

Figure 3:
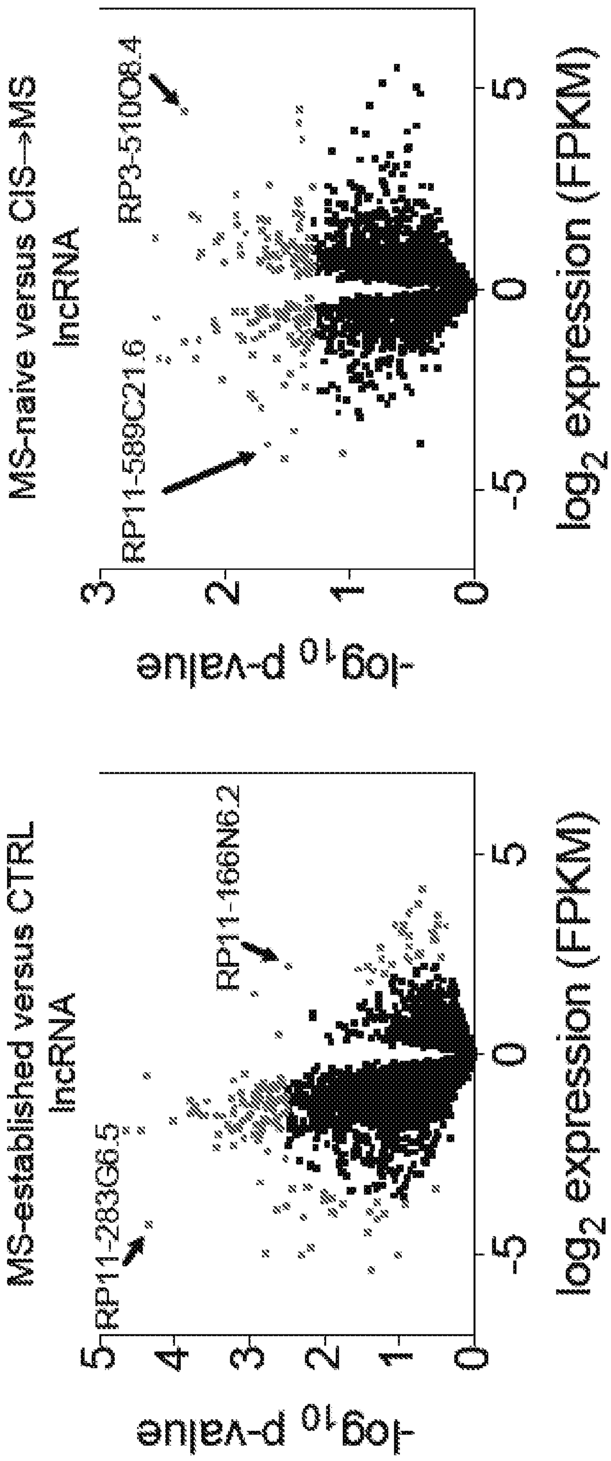
FIG. 3 shows differential expression of unique lncRNAs between MS, control, and distinct stages of MS.
Figure 4:
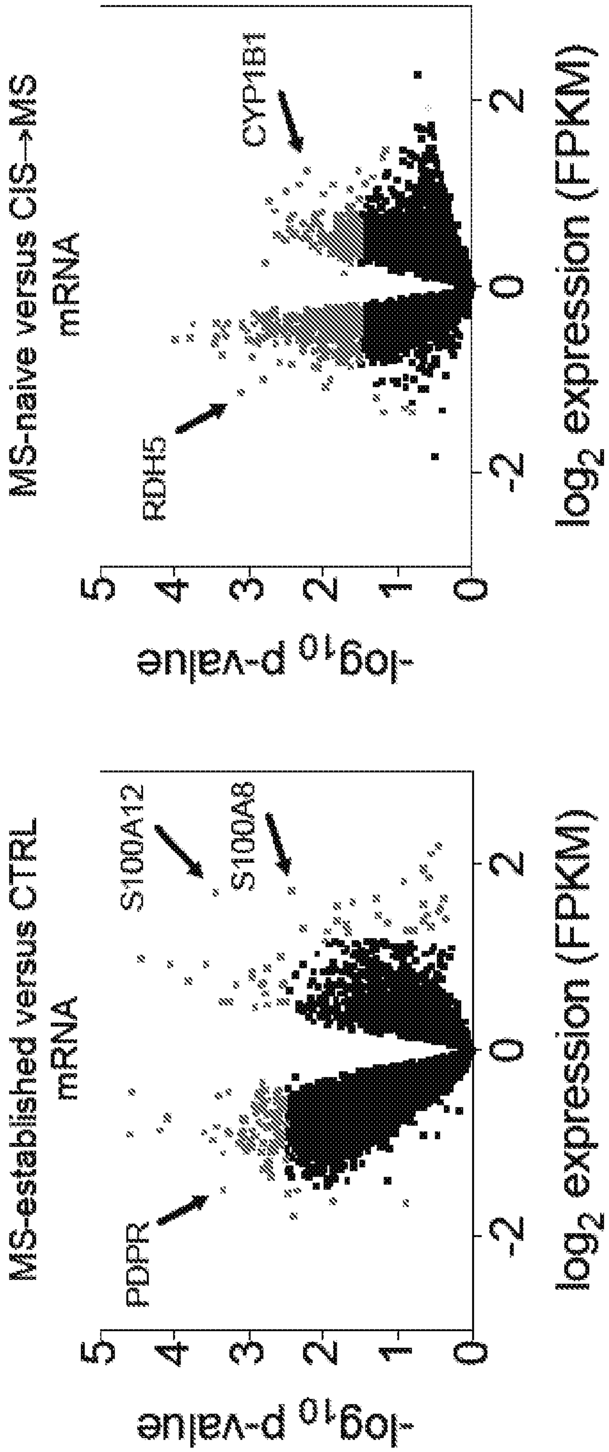
FIG. 4 shows differential expression of unique mRNAs between MS, control, and distinct stages of MS.
Figure 5:
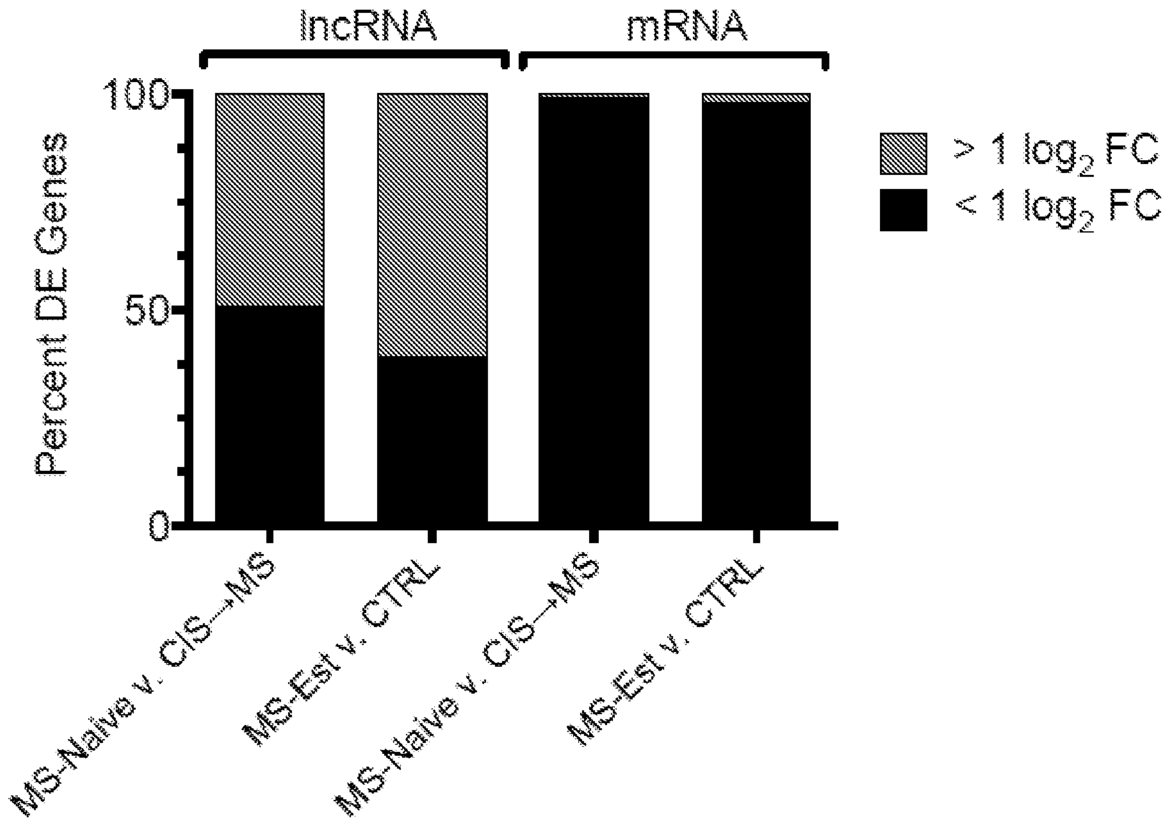
FIG. 5 shows magnitude of fold-change differences across mRNA and lncRNA species at distinct stages of multiple sclerosis.

Volcano plots are shown in FIG. 3 and FIG. 4 to illustrate the differences in fold-change gene expression (X-axis) versus significance for an individual gene (Y-axis) (FIG. 1). Expression patterns of lncRNAs (FIG. 3) and mRNAs (FIG. 4) were compared in (1) healthy control subjects versus the MS-established cohort and (2) MS-naïve versus the CIS→MS cohort. Y-axes are $log_{10}$ p-values and x-axes are expression ratios, $log_2$. Comparison of the $log_2$ fold-change differences in healthy control versus MS-established found 1,859 differentially expressed mRNAs and 752 annotated lncRNAs. In the MS-naïve versus the CIS→MS cohort, 818 mRNAs and 149 annotated lncRNAs were differentially expressed. Differences in expression of lncRNAs were found that ranged in magnitude from 22 to 25 or 4-fold to 32-fold in the different cohorts while differences in expression of mRNAs were typically <22 or <4-fold. Additional analysis of the differentially expressed lncRNAs and mRNAs assessed using DESeq2 found that 49% and 61% of the lncRNAs in the MS-Naïve versus MS→CIS and MSestablished versus CTRL cohorts, respectively, had greater than a 2-fold change in gene expression (FIG. 5). In contrast, only ~1% and 2% of the mRNAs in the same cohorts exhibited a 2-fold change or greater in mRNA expression levels. Plots in FIG. 5 show the percentage of differentially expressed (DE) species as a function of >1 or <1 fold change expression ratios, $log_2$, across annotated lncRNAs (left) and mRNAs (right). Differentially expressed species all have an adjusted p value<0.05 for across two experimental comparisons: (1) MSNaïve versus CIS→MS and (2) MS-established versus healthy control (CTRL) subjects. Accordingly, the lncRNA expression profile was determined to be more dynamic than the mRNA expression profile across the subjects examined using whole genome RNA sequencing. Therefore, lncRNA levels have greater ability to discriminate between case and control cohorts as well as case and disease control cohorts and can produce tests with improved capacity to classify disease and control groups.

Example 2

Figure 6:
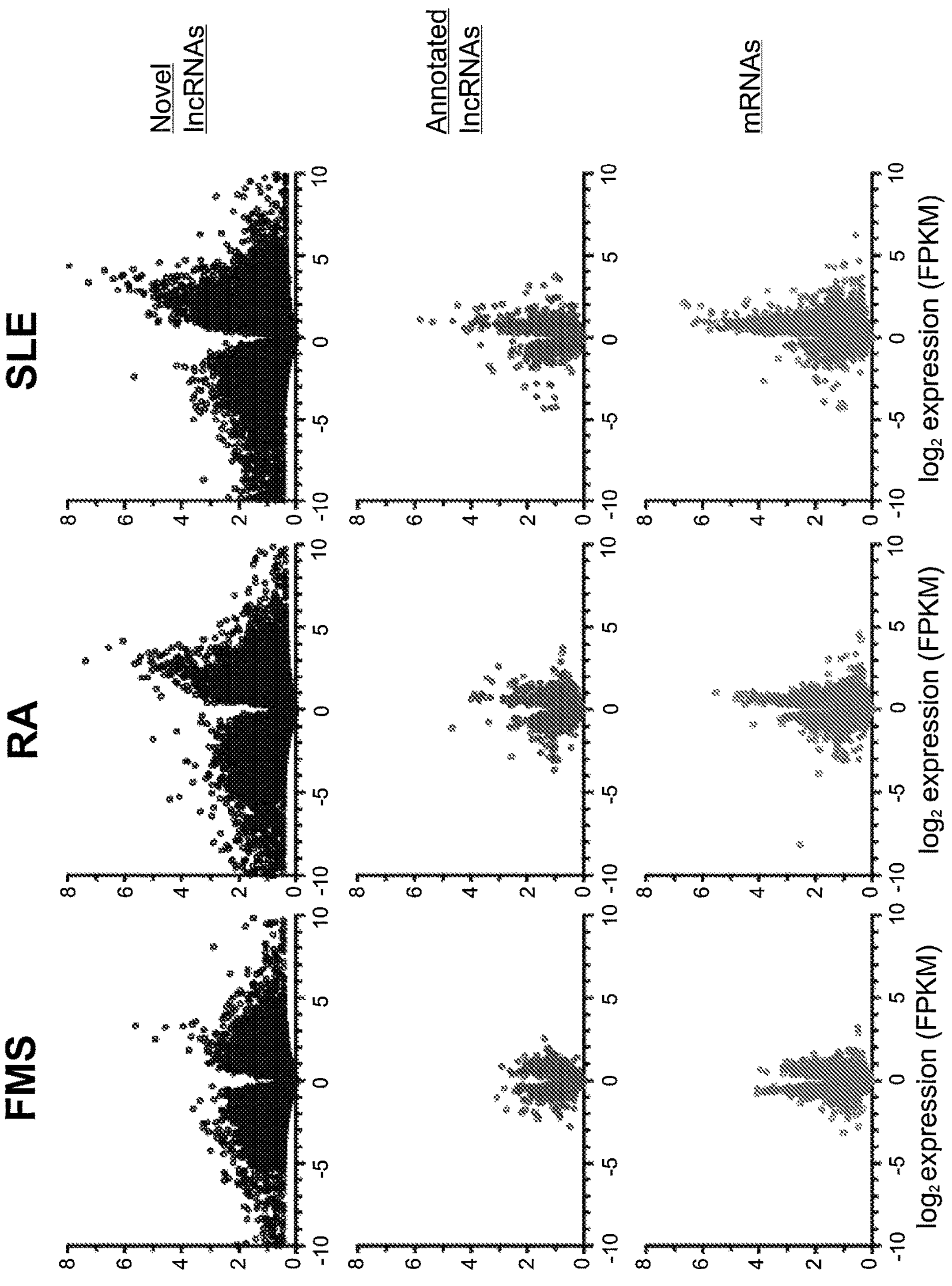
FIG. 6 shows Differential expression of novel lncRNAs, annotated lncRNAs, and mRNAs in FMS, RA, and SLE.

Peripheral whole blood was collected into PAXgene tubes from healthy control subjects (N=8), and subjects diagnosed with FMS (n=6), RA (n=6), or SLE (n=6). Subjects included in these cohorts had bloods sample obtained at the time of diagnosis. Subjects were subsequently tracked using electronic medical records for a period of 3 years and the diagnoses did not change. Total RNA from PAXgene tubes was used to prepare sequencing libraries using the Illumina Tru-Seq RNA kit with oligo-dT as the primer. 100 bp paired-end reads were generated with an Illumina Hi-Seq 2500. A quality control step was initially performed using tools such as Fastx Toolkit and FastQC. The RNA data were aligned with TopHat2 and gene expression levels were quantified using Cufflinks and are reported as FPKM (fragments per kilobase per million reads). Differentially expressed species were determined using DESeq2. False discovery rate (FDR<0.05) was used for multiple test correction. GTF files for mRNAs and annotated mRNAs were obtained from GENCODE (release 19; GRCh37. p 13). Novel lncRNAs were identified using established methodologies (36). A 0.5 FPKM cutoff was used for lncRNAs and mRNAs across these sequencing data. Volcano plots were used to illustrate differences in fold-change gene expression (X-axis) versus significance for an individual gene (Y-axis) (FIG. 6). Expression patterns of novel lncRNAs (FIG. 6; top two plots), annotated lncRNAs (FIG. 6; middle two plots), and mRNAs (FIG. 6; bottom two plots) were compared in (1) healthy control subjects versus the FMS cohort, (2) healthy controls versus RA, (3) healthy controls versus SLE, (4) FMS versus RA, (5) FMS versus SLE, and (6) RA versus SLE (4-6 not shown). Composites of differentially expressed novel lncRNAs, annotated lncRNAs, and mRNAs across these comparisons is shown in FIG. 6. Plots shown in FIG. 6 are the percentage of differentially expressed (DE) species as a function of >2 or <2 fold change (FC) expression ratios, $log_2$, mRNAs (left), annotated lncRNAs (middle) and novel lncRNAs (right). Differentially expressed species all have an adjusted p value<0.05 across six experimental comparisons. *=p<0.05 comparing lncRNAs>2 $log_2$ FC to mRNAs>2 $log_2$ FC.

Figure 7:
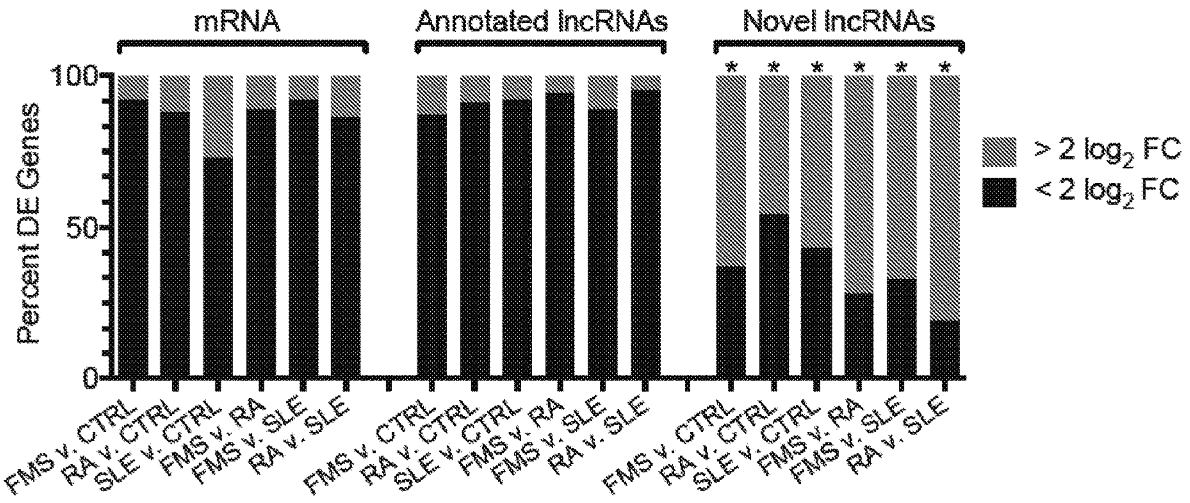
FIG. 7 shows magnitude of fold-change differences across mRNA and lncRNA species in FMS, RA, and SLE.

Comparison of the $log_2$ fold-change differences across these cohorts resulted in identification of 389 mRNAs and 3,317 lncRNAs (FMS vs. CTRL); 1,015 mRNAs and 1,538 lncRNAs (RA vs. CTRL); 2,003 mRNAs and 1,394 lncRNAs (SLE vs. CTRL); 542 mRNAs and 2,193 lncRNAs (FMS vs. RA); 467 mRNAs and 2,203 lncRNAs (FMS vs. SLE); and 632 mRNAs and 3,107 lncRNAs (RA vs. SLE). Differences in expression of lncRNAs ranged in magnitude from 22 to 210 or 4-fold to 1000-fold in the different cohorts while differences in expression of mRNAs were typically <22 or <4-fold. Additional analysis of the differentially expressed lncRNAs and mRNAs assessed using DESeq2 found that 63%, 46%, 57%, 72%, 67%, and 81% of the lncRNAs in the FMS vs. CTRL, RA vs. CTRL, SLE vs. CTRL, FMS vs. RA, FMS vs. SLE, and RA vs. SLE comparisons, respectively, had greater than a 4-fold difference in gene expression (FIG. 7). In contrast, only 8%, 12%, 27%, 11%, 8%, and 14% of the mRNAs in the same cohorts exhibited a 4-fold difference or greater in mRNA levels. Thus, lncRNA expression profiles were more dynamic than mRNA expression profiles across the subjects examined using whole genome RNA sequencing. Therefore, lncRNA levels have greater ability to discriminate between case and control cohorts as well as case and disease control cohorts and we will be able to produce tests with improved capacity to classify disease and control groups.

Example 3

From RNA-seq analysis of the expression results obtained in Example 1, about 190 candidate lncRNAs differentially expressed between one, two or three MS cohorts and CTRL were identified. Primer pairs were designed for each lncRNA. Those candidate lncRNAs were then evaluated using RT-PCR. The following selection criteria was used: (1) average cycle threshold, Ct, <32 after RNA isolation from a cell sample, cDNA synthesis and PCR amplification, (2) amplicon was a single band detected on agarose gels of the correct size, (3) coefficient of variance<2.0 among multiple replicates (standard deviation/mean) and (4) amplicon sequence verification. Reproducibility of replicates has been found to suffer in mRNA differential expression analysis if the Ct>32. Coefficient of variance (C.V.) is another indicator of this but it is also an indicator of primer efficiency.

From the above analyses, 46 lncRNAs were identified for which the differential expression was measured among MS cohorts and CTRL (Table 4).

The ENSEMBL gene identifier number is shown in the left column and Average expression (29) of each lncRNA in a cell line (Jurkat) is shown in the next column followed by the coefficient of variance (C.V.). All amplicon sequences were successfully verified. Ratios are CASE/CTRL means, $\log_2$: number of subject samples; CTRL, N=80; MS-C, N=40; MS-N, N=40; MS-E, N=100. Q-values were determined and bold numbers designate values that were found to be statistically significant after correction for false discovery rates using Benjamini-Hochberg correction methods.

All samples were treated as follows: 1) after obtaining informed consent, blood was collected from subjects into PAXgene tubes (PAXgene tubes were stored according to manufacturer's guidelines), 2) total RNA was purified using PAXgene RNA isolation kits, 3) RNA amounts were measured using a Nanodrop spectrophotometer, 4) cDNA synthesis was performed using oligo-dT primers and Superscript 3 (Invitrogen), 5) PCR reactions were performed in 384-well plates in 10 microliter volumes containing 1 ng/μl cDNA, Taqman master mix and SYBR green.

Expression levels of these lncRNAs were compared in the different RRMS cohorts, MS-C, MS-N, and MSE to CTRL using GAPDH expression for normalization using the formula, $2^{(GAPDH\ Ct\text{-}test\ Ct)}$. Results were expressed as the ratio between the disease cohorts and CTRL cohorts, $\log_2$. In general, most lncRNAs were under-expressed rather than over-expressed in the MS cohorts compared to CTRL cohorts. Some lncRNAs were under-expressed by over 16-fold in at least one MS cohort compared to the control cohort. Differential expression of many of the lncRNAs was similar in the different MS cohorts compared to the CTRL cohort. However, some lncRNAs were differentially expressed in only one or two MS cohorts compared to the CTRL cohort. This is consistent with MS disease progression in which inflammatory processes are most pronounced early in the disease and may indicate a role for certain lncRNAs in the inflammatory processes.

Example 4

Figure 8:
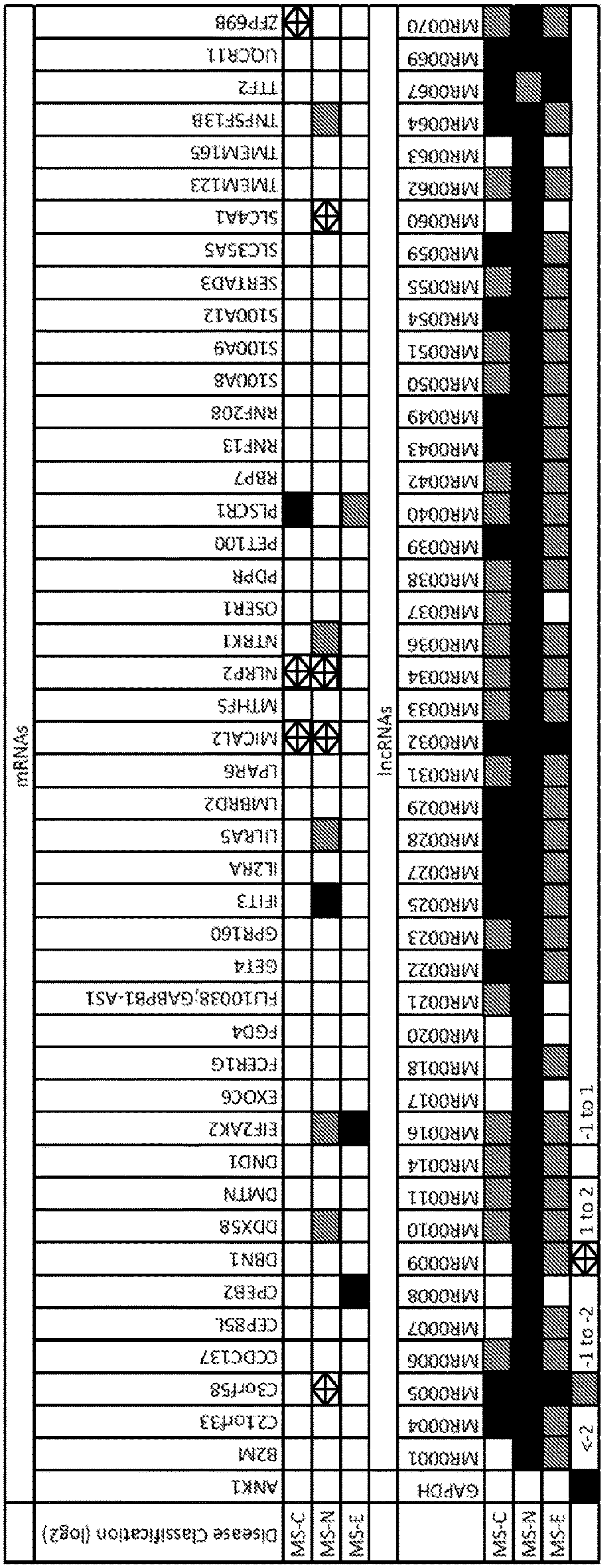
FIG. 8 shows levels of differential expression of select mRNAs and lncRNAs between indicated MS cohorts and CTRL cohorts.

To confirm that lncRNAs display greater differential expression between CASE/CTRL cohorts than mRNAs, whole genome RNA-seq was performed to identify differentially expressed mRNAs in blood in cohorts of CTRL (N=8), MS-C(N=6), MS-N(N=6), MS-E (N=8). 46 target mRNAs were picked and GAPDH was included as a housekeeping gene. TLDA plates cards were designed and expression of the target mRNAs was analyzed in a larger cohort of about 1200 subjects including healthy controls, disease controls and subjects with MS. Testing machine learning algorithms were developed from this dataset. From the RNA-seq analysis, candidate lncRNAs were identified as described above. Levels of differential expression of the mRNAs were compared to lncRNAs selected from the RNA-seq experiment in larger cohorts to. To do so, the heatmap shown in FIG. 8 illustrates the level of differential expression of the selected mRNAs and lncRNAs in each MS cohort compared to the CTRL cohort. Results are expressed as case/control ratios, $\log_e$ and represented as shown in the legend of FIG. 8 (<−2, −1 to −2, 1 to 2, or −1 to 1). LncRNA expression data were as shown in Table 4. The results demonstrate that levels of differential expression of the selected lncRNAs was much greater than the levels of differential expression of the selected mRNAs in these same MS samples.

Example 5

Figure 12:
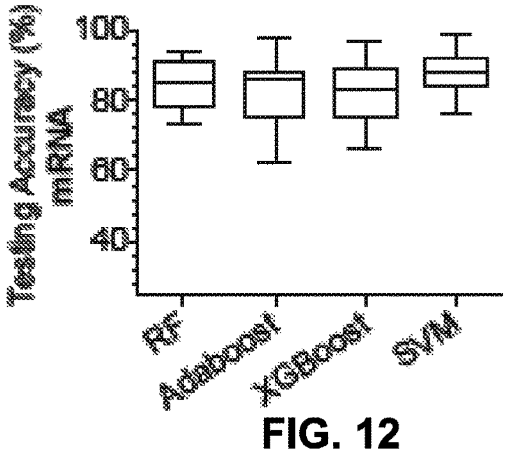
FIG. 12 depicts the testing accuracy of the machine learning methods for mRNA.
Figure 14:
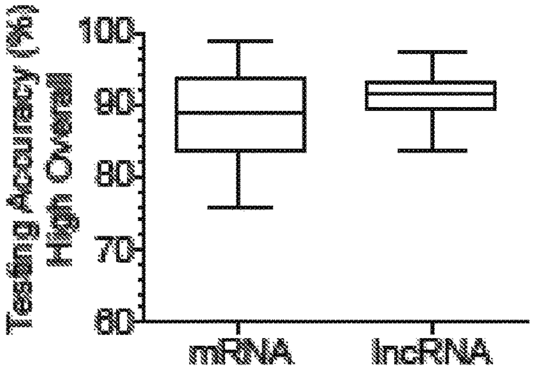
FIG. 14 depicts the highest overall testing accuracies.
Figure 13:
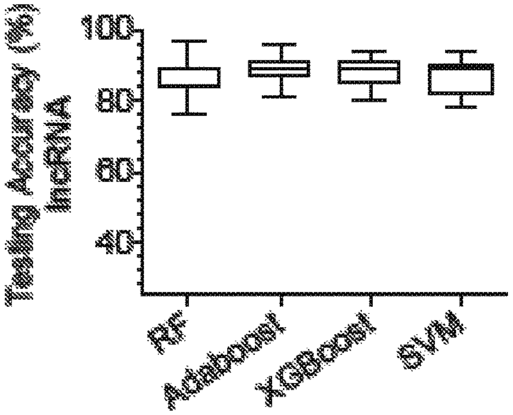
FIG. 13 depicts the testing accuracy of the machine learning methods for IncRNA.
Figure 15:
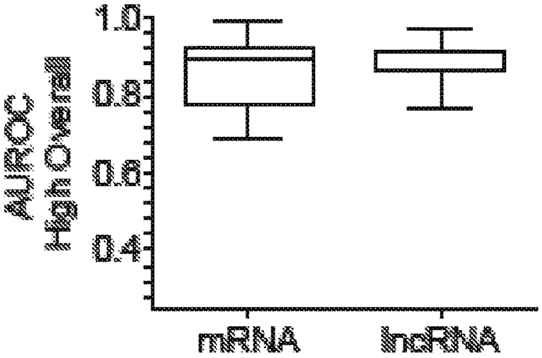
FIG. 15 depicts the AUROC of the application overall for both mRNA and IncRNA.

Peripheral whole blood samples were obtained for a population of 1,009 cases comprising CTRL, healthy subjects with no family history of autoimmune disease; CTRL-UFM, unaffected family members of subjects with MS; CISMS, subjects with a clinically isolated syndrome (CIS) who received a formal diagnosis of MS at a later date; MS-NAIVE, patients with a diagnosis of MS prior to the initiation of therapies; MS-EST, subjects with established MS on medicines; OND, other neurologic disease, inflammatory (I) or non-inflammatory (NI). Whole genome RNA sequencing and data analysis was applied using methods described above to identify both differentially expressed lncRNAs and mRNAs. A ratioscore algorithm (as described above) was applied to pairs of differentially expressed lncRNAs and pairs of differentially expressed mRNAs to generate input data for machine learning systems. 21 binary comparisons were performed separately using mRNA and lncRNA expression as shown in FIG. 11 using 75% of the dataset for training and 25% for validation testing. Random Forests, AdaBoost, XGBoost, and SVM were each trained as binary classifiers and evaluated on the validation data. FIG. 11 shows the number of ratios and accuracies for each binary comparison using the ratioscore algorithm and the highest overall accuracies obtained from one of four machine learning classifiers: random forest (RF), AdaBoost, XGBoost, or support vector machine (SVM) with the validation testing set using mRNA (left column) or lncRNA (right column) data. The area under receiver operator characteristic (ROC) curves were also determined for the machine learning methods that produced the best overall accuracy according to each case/control comparison. FIG. 12 and FIG. 13 are box and whisker plots showing validation testing accuracies for each binary comparison using four machine learning classifiers with mRNA data (FIG. 12) or lncRNA data (FIG. 13). FIG. 14 and FIG. 15 are box and whisker plots depicting highest overall testing accuracies (FIG. 14) and area under the ROC curves (FIG. 15) using the validation testing set.

Example 6

Figure 17:
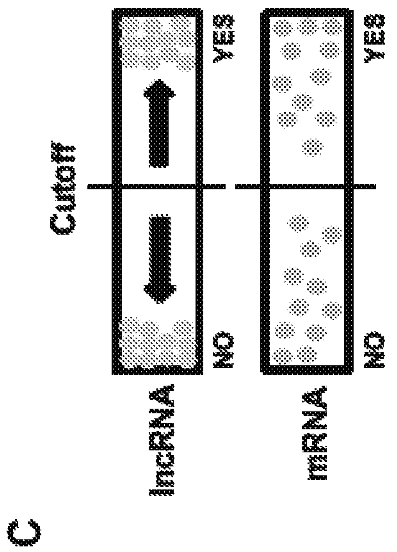
FIG. 17 diagrams trends in confidence of MS machine learning predictions of lncRNA and mRNA species
Figure 16:
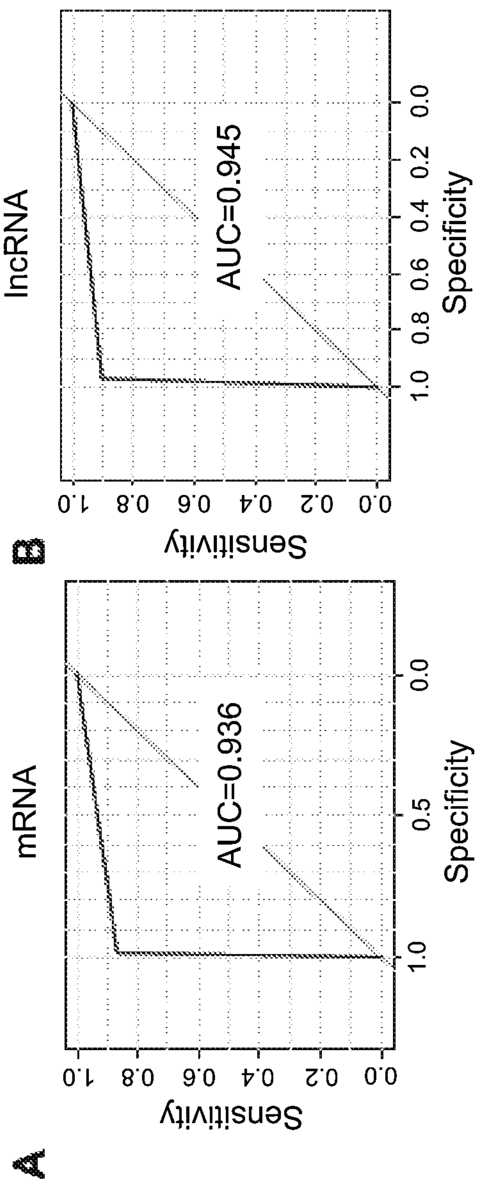
FIG. 16 compares optimized multi-category or hybrid classifiers for mRNAs and lncRNAs.

Binary classification inputs derived from CTRL, CTRL-UFM (unaffected family members of subjects with MS), MS (subjects with a clinically isolated syndrome (CIS) who received a formal diagnosis of MS at a later date), OND-I (other inflammatory neurological conditions), or OND-NI (other non-inflammatory neurological conditions) subjects were used as inputs to train and test different combinations of machine learning methods capable of multi-class discrimination (e.g., hybrid classifiers as described above). FIG. 16 through FIG. 18 show results of the application of the trained hybrid classifier to a test data set for used for validation. FIG. 16 shows ROC curves and calculated area under the ROC curve values for optimal multi-category classifier combinations capable of discriminating MS vs. CTRL or OND using mRNA (A) or lncRNA (B) datasets. FIG. 17 is a diagram illustrating trends in confidence of MS machine learning predictions using lncRNA and mRNA gene expression datasets. FIG. 18 summarizing accuracy, sensitivity, and specificity of MS, OND-I, or OND-NI multi-category classifiers using the validation testing set.

Example 7

Differential gene expression analysis of gastrointestinal cancer subjects versus healthy control subjects was performed using methods and systems of the invention. Table 5 provides the 46 genes that were study, of which 43 are statistically significant. Bolded values in Table 5 signifies those values statistically significant after correction for false discover rates using Benjamini-Hochberg correction method. This analysis suggests that differential gene expression may be used to monitor disease and therapeutic efficacy using the methods and systems disclosed herein.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

TABLE 1

Primers targeting lneRNAs in FMS

| Target lncRNA gene (IQuity ID) | Forward Primer | Reverse Primer |
|---|---|---|
| RH002 | SEQ ID NO 1: AAGGCACAGAGCCAAGAAGT | SEQ ID NO 2: CAGTGCCCAGAGCTATGCTT |
| RH003 | SEQ ID NO 3: TGGTTGTCAGGGGATAGGAG | SEQ ID NO 4: CTGTCACCACCATTGAGCAC |
| RH004 | SEQ ID NO 5: GGGGACCAAAAACTGTCAGA | SEQ ID NO 6: GCATGATCAAATCATCCCCTA |
| RH006 | SEQ ID NO 7: CTGGCCTCTGACATGAACAA | SEQ ID NO 8: AGCTGCCCATTGCATCTATT |
| RH008 | SEQ ID NO 9: ATCCACAGGGGTCACAGC | SEQ ID NO 10: GAGGGCCAATGGGAACTT |
| RH010 | SEQ ID NO 11: GGCAGGACCACAGTGATGAT | SEQ ID NO 12: CAATTCGCCATGTCTCTCTG |
| RH011 | SEQ ID NO 13: GCATTAAGGAGCCCACAGAG | SEQ ID NO 14: ACCTGGCTCCACCTCCTACT |
| RH012 | SEQ ID NO 15: GAGGTTGGAGGATCACTTGG | SEQ ID NO 16: TCTGGGTGGGTTCATTTCTC |
| RH013 | SEQ ID NO 17: TTCTTTTCAAAGTCGTGTGGA | SEQ ID NO 18: TGGATGGAAAATTGTGAGCA |
| RH014 | SEQ ID NO 19: CGCCTCAGCCTTCTAAAGTG | SEQ ID NO 20: ACTCTCCAGAGTGGCACCAG |
| RH015 | SEQ ID NO 21: TCACGATTCAGTCGCAATTC | SEQ ID NO 22: CACAGAGCAGGGCATAATGA |
| RH017 | SEQ ID NO 23: TGCTCATGGAGCAGAATCAG | SEQ ID NO 24: TCTTCCCACCAGGAAATCAC |

TABLE 2

| Primers targeting lncRNAs in RA | | |
|---|---|---|
| Target lncRNA species (IQuity ID) | Forward Primer | Reverse Primer |
| RH018 | SEQ ID NO 25: TCACCCACTACCCTCTCCTG | SEQ ID NO 26: TGAAATGTGGCATTCCTACG |
| RH019 | SEQ ID NO 2: CATGGGGCTATTTGGAGAAA | SEQ ID NO 28: CACCACTGGTTCCTGGCTAT |
| RH020 | SEQ ID NO 29: GGGCTTGAACTTTGGTTCTG | SEQ ID NO 30: GTTGGGGAGGAGCCTATGAT |
| RH022 | SEQ ID NO 31: CTGGAAAATTGAAAGAACAGACA | SEQ ID NO 32: TTCTTTTTCCTTATGCTATGTTGC |
| RH023 | SEQ ID NO 33: CCACGTGTATCAAGAGACATCA | SEQ ID NO 34: TTTGATGCCCTTATCATTCC |
| RH024 | SEQ ID NO 35: TGGATATTTGGTCTGCGTAGTG | SEQ ID NO 36: CAGGCTGGTCTCAAAGTCCT |
| RH025 | SEQ ID NO 37: GAGAATGCTCCTGCCTCATC | SEQ ID NO 38: CCAGGTGCACAAAGAAATCA |
| RH026 | SEQ ID NO 39: TGCGGCTGGAGGAGTTAATA | SEQ ID NO 40: CGCCTCTCTCTTCCTGTCTC |
| RH029 | SEQ ID NO 41: CTTCCCTCGTTTCTTTGCTG | SEQ ID NO 42: ACCTCTCCTGGCCCTATGAT |
| RH030 | SEQ ID NO 43: GAACAGGGGAAGGGAGAAAG | SEQ ID NO 44: GCCACCAAAGGCTATACCAA |
| RH031 | SEQ ID NO 45: CAGGAAGAAGTGCATGTTGG | SEQ ID NO 46: AGAGCTCTGGGAGGGACAC |
| RH032 | SEQ ID NO 47: CCCAGGGGTCTGATAATTCA | SEQ ID NO 48: ATGCATAGGGGACGAAAACA |
| RH033 | SEQ ID NO 49: CTTTGCCCCACCTTTAAACA | SEQ ID NO 50: ATAGCATGTGATGGGGCTTC |
| RH035 | SEQ ID NO 51: AAGCTATGTGAAGCATTTTGAGC | SEQ ID NO 52: CCAGCCAAGGTCTCCTCTTT |
| RH036 | SEQ ID NO 53: CCTGTAGTCCCTCCAAGCAG | SEQ ID NO 54: GCTGTGTGTTCCAGGTGAGA |
| RH038 | SEQ ID NO 55: CAATGGCTGTTTCATCCTCA | SEQ ID NO 56: CCTTACTGGGTGACAGGAAAA |

TABLE 3

| Primers targeting lncRNAs in SLE | | |
|---|---|---|
| Target lncRNA species (IQuity ID) | Forward Primer | Reverse Primer |
| RH039 | SEQ ID NO 57: TTTTGTGCTTCTCTGCCAAG | SEQ ID NO 58: TGTGTGCAAACTAAGTGCCAAT |
| RH040 | SEQ ID NO 59: TGGCTTGGAGAAAGGAGAGA | SEQ ID NO 60: GGCAAAAGGAAGTCCATTCA |
| RH041 | SEQ ID NO 61: TTTTCCCAAATCCCAATCAA | SEQ ID NO 62: ACAACCGGGGTTCTTTTACC |
| RH043 | SEQ ID NO 63: GGTGGAAACCTGACAAATGG | SEQ ID NO 64: CCAGGAAGGTCAGATTCCAA |
| RH044 | SEQ ID NO 65: GCTGGGTACGGTAAAGGACA | SEQ ID NO 66: CTGGGAAAGGAACACCTGAA |

TABLE 3-continued

| Primers targeting lncRNAs in SLE | | |
|---|---|---|
| Target lncRNA species (IQuity ID) | Forward Primer | Reverse Primer |
| RH045 | SEQ ID NO 67: GGTTGAGGCCACTGCTTTAC | SEQ ID NO 68: CCCAGCTGAAGAGATTGGAA |
| RH046 | SEQ ID NO 69: TTTCCCTGTGTCTTCCATCC | SEQ ID NO 70: AAAAGCTGCAGAAGCCAGAG |
| RH047 | SEQ ID NO 71: TTTTTCTTGGATGCCTGGAC | SEQ ID NO 72: ATCTCTCCCTCCCCAAGTGT |
| RH049 | SEQ ID NO 73: TGCCCACACTGTTTATTGCT | SEQ ID NO 74: CACTTTGGGAGGAACTCGAA |
| RH050 | SEQ ID NO 75: GTAGGGGCTGTCCGTATCAA | SEQ ID NO 76: ATTTCCCCACAGCTCTTCCT |
| RH051 | SEQ ID NO 77: ACAGATGCTGCCCTCTGTG | SEQ ID NO 78: AAGCCCAGGACTCTCCTCAT |
| RH053 | SEQ ID NO 79: AGTGAAACAGCCAGTGCAAA | SEQ ID NO 80: CTGGTTGCTCTGCTCTACCC |
| RH054 | SEQ ID NO 81: GTATGGTGCACTGGGGATTC | SEQ ID NO 82: CCCCTTCCTATGCCTCAAAG |
| RH055 | SEQ ID NO 83: TAGGTGAAAATGCCCCAAAA | SEQ ID NO 84: CATTTCGCTGAAGCTTGTGT |
| RH057 | SEQ ID NO 85: CCATGCAATGATTGTTTTGC | SEQ ID NO 86: CAAATGTGTATGTTTGTATGGTGGT |
| RH058 | SEQ ID NO 87: TCCTTTTTGTAATGGGAAGTGAA | SEQ ID NO 88: TACGTGTAGCCCCACCTAAG |
| RH059 | SEQ ID NO 89: TGTCCTCAAAACCCACACAA | SEQ ID NO 90: AGAGCGCGTGTGAGACTGTA |
| RH061 | SEQ ID NO 91: AGAATTTGCTGCCTGCTTGT | SEQ ID NO 92: GCTGGGGAGGTAAAGTGAAA |

TABLE 4

| Differentially Expressed lncRNA species in MS | | | | | |
|---|---|---|---|---|---|
| LncRNA gene ensembl identifier | avg. Ct | C.V. | MS-C/CTRL ($log_2$ ratio) | MS-N/CTRL ($log_2$ ratio) | MS-E/CTRL ($log_2$ ratio) |
| ENSG00000111640 (GAPDH) | 15.57 | 0.30 | 0.02 | 0.02 | 0.00 |
| ENSG00000272288 | 21.80 | 0.32 | −0.74 | −3.82 | −1.24 |
| ENSG00000237017 | 26.25 | 0.40 | −3.27 | −4.03 | −1.93 |
| ENSG00000237017 | 31.37 | 1.20 | −4.23 | −4.12 | −2.23 |
| ENSG00000249096 | 25.81 | 0.42 | −1.61 | −3.61 | −1.39 |
| ENSG00000271870 | 22.30 | 0.62 | 0.17 | −3.53 | −1.33 |
| ENSG00000272579 | 20.18 | 0.11 | 0.90 | −2.88 | −0.87 |
| ENSG00000233223 | 23.73 | 0.26 | −0.90 | −3.62 | −1.35 |
| ENSG00000267321 | 22.84 | 0.22 | −1.06 | −3.85 | −1.35 |
| ENSG00000267321 | 25.54 | 0.41 | −1.70 | −4.00 | −1.74 |
| ENSG00000263065 | 27.73 | 0.85 | −1.45 | −4.10 | −1.68 |
| ENSG00000228395 | 24.72 | 0.52 | −1.78 | −3.96 | −1.76 |
| ENSG00000264304 | 24.96 | 0.59 | 0.68 | −2.96 | −0.01 |
| ENSG00000261207 | 25.31 | 0.50 | −0.71 | −3.82 | −1.46 |
| ENSG00000245060 | 26.59 | 0.37 | 0.83 | −2.69 | −0.36 |
| ENSG00000228140 | 28.30 | 0.57 | −1.59 | −2.01 | 0.11 |
| ENSG00000228140 | 27.11 | 0.33 | −2.78 | −3.44 | −1.27 |
| ENSG00000261346 | 27.34 | 0.73 | −1.43 | −3.74 | −1.63 |
| ENSG00000242258 | 26.62 | 0.69 | −2.79 | −3.95 | −1.74 |
| ENSG00000272462 | 24.83 | 0.45 | −1.97 | −3.29 | −1.07 |
| ENSG00000272462 | 24.31 | 0.54 | −2.59 | −3.96 | −1.81 |
| ENSG00000225963 | 24.75 | 0.37 | −3.33 | −4.40 | −1.87 |
| ENSG00000267194 | 23.75 | 0.63 | −1.41 | −3.35 | −1.54 |

TABLE 4-continued

Differentially Expressed lncRNA species in MS

| LncRNA gene ensembl identifier | avg. Ct | C.V. | MS-C/CTRL ($log_2$ ratio) | MS-N/CTRL ($log_2$ ratio) | MS-E/CTRL ($log_2$ ratio) |
|---|---|---|---|---|---|
| ENSG00000260219 | 25.00 | 0.55 | −2.63 | −4.19 | −1.99 |
| ENSG00000260219 | 24.96 | 0.50 | −1.59 | −3.87 | −1.50 |
| ENSG00000237424 | 21.30 | 0.39 | −1.09 | −3.65 | −1.23 |
| ENSG00000249684 | 29.28 | 0.45 | −1.43 | −3.62 | −1.56 |
| ENSG00000273265 | 26.19 | 0.88 | −1.15 | −3.42 | −0.84 |
| ENSG00000273265 | 24.91 | 0.85 | −1.38 | −3.64 | −1.26 |
| ENSG00000256072 | 25.37 | 0.21 | −3.85 | −4.16 | −1.77 |
| ENSG00000272955 | 27.12 | 0.77 | −1.11 | −3.07 | −1.73 |
| ENSG00000251580 | 23.95 | 0.38 | −1.31 | −3.44 | −1.17 |
| ENSG00000272782 | 26.61 | 0.48 | −2.07 | −3.89 | −1.62 |
| ENSG00000260496 | 29.31 | 0.62 | −4.19 | −4.12 | −1.69 |
| ENSG00000260496 | 29.01 | 1.67 | −1.23 | −3.86 | −1.35 |
| ENSG00000271122 | 22.90 | 0.57 | −1.65 | −4.23 | −1.56 |
| ENSG00000223768 | 21.54 | 0.14 | −2.40 | −4.09 | −1.80 |
| ENSG00000223768 | 22.55 | 0.97 | −1.50 | −4.10 | −1.81 |
| ENSG00000262312 | 27.07 | 0.55 | −2.00 | −4.05 | −1.76 |
| ENSG00000244879 | 22.74 | 0.63 | 0.67 | −3.16 | −0.67 |
| ENSG00000223396 | 22.06 | 0.27 | −1.68 | −3.76 | −1.37 |
| ENSG00000257270 | 21.65 | 0.53 | −0.13 | −2.96 | −0.82 |
| ENSG00000258768 | 24.67 | 0.39 | −3.16 | −4.14 | −1.70 |
| ENSG00000243368 | 26.50 | 1.53 | −3.06 | −1.61 | −2.15 |
| ENSG00000224888 | 27.88 | 0.59 | −2.91 | −3.96 | −2.07 |
| ENSG00000258302 | 23.68 | 0.47 | −1.39 | −3.95 | −1.55 |

TABLE 5

Differentially Expressed Genes in Gastrointestinal Cancer

| Gene ID | Internal ID | Avg Ct | q-value | minus log(10) q-value | Log2 ratio v. CTRL |
|---|---|---|---|---|---|
| RP11-245J9.6 | GIL0001 | 28.5 | 0.0195 | 1.7 | 0.9 |
| RP11-342M1.3 | GIL0002 | 31.5 | 0.0000 | 4.9 | 1.3 |
| RP11-3P17.5 | GIL0003 | 31.7 | 0.0000 | 5.0 | 1.5 |
| AC006547.15 | GIL0004 | 30.0 | 0.0004 | 3.4 | 1.8 |
| RP11-443B7.3 | GIL0005 | 30.8 | 0.0017 | 2.8 | 1.1 |
| RP11-666A8.8 | GIL0007 | 29.8 | 0.0002 | 3.6 | 1.4 |
| LINC00570 | GIL0008 | 32.3 | 0.0001 | 4.1 | 1.6 |
| AC093415.2 | GIL0009 | 30.6 | 0.0002 | 3.8 | 1.3 |
| RP3-337H4.9 | GIL0012 | 30.2 | 0.0000 | 5.2 | 1.5 |
| RP11-49619.1 | GIL0013 | 31.0 | 0.0001 | 3.8 | 2.1 |
| RP11-192H23.8 | GIL0014 | 29.0 | 0.0000 | 4.3 | 1.8 |
| CTB-129O4.1 | GIL0015 | 27.6 | 0.0000 | 4.3 | 1.7 |
| RP11-513M16.8 | GIL0016 | 28.3 | 0.0001 | 4.2 | 1.5 |
| RP11-70C1.1 | GIL0017 | 28.3 | 0.0000 | 4.3 | 1.4 |
| RP4-65E18.8 | GIL0018 | 27.6 | 0.0006 | 3.2 | 1.4 |
| RP11-148K1.12 | GIL0019 | 29.7 | 0.0020 | 2.7 | 1.4 |
| RP4-647J21.1 | GIL0021 | 27.0 | 0.0127 | 1.9 | 1.1 |
| RP5-1092A3.4 | GIL0022 | 29.5 | 0.0000 | 5.2 | 2.0 |
| RP11-140K17.3 | GIL0024 | 29.4 | 0.0000 | 5.6 | 2.5 |
| LINC00493 | GIL0025 | 26.6 | 0.0001 | 3.8 | 2.1 |
| RP11-256L6.3 | GIL0026 | 26.7 | 0.0426 | 1.4 | 0.9 |
| LINC00211 | GIL0027 | 28.1 | 0.0097 | 2.0 | 1.0 |
| RP1-55C23.7 | GIL0028 | 27.1 | 0.2315 | 0.6 | 0.6 |
| RP11-351124.1 | GIL0029 | 29.2 | 0.0108 | 2.0 | 1.2 |
| RP5-1142A6.2 | GIL0030 | 30.1 | 0.0008 | 3.1 | 1.3 |
| IGBP1-AS1 | GIL0031 | 30.6 | 0.0000 | 7.7 | 1.8 |
| RP1-20N2.6 | GIL0032 | 29.8 | 0.0000 | 6.7 | 1.7 |
| RP11-326G21.1 | GIL0034 | 29.5 | 0.0227 | 1.6 | 1.0 |
| RP11-430C7.4 | GIL0036 | 27.6 | 0.0030 | 2.5 | 1.5 |
| RP11-148021.2 | GIL0037 | 29.6 | 0.0002 | 3.7 | 1.4 |
| RP11-264B17.4 | GIL0038 | 27.4 | 0.0035 | 2.5 | 1.5 |
| RP11-7218.1 | GIL0039 | 31.3 | 0.0006 | 3.2 | 1.4 |
| RP11-379H18.1 | GIL0040 | 30.5 | 0.0001 | 4.0 | 1.8 |
| RP3-368A4.5 | GIL0043 | 27.6 | 0.1479 | 0.8 | 0.6 |
| AC007743.1 | GIL0044 | 32.0 | 0.0000 | 5.4 | 1.2 |
| RP11-876N24.5 | GIL0046 | 29.7 | 0.0000 | 5.2 | 1.9 |
| MATN1-AS1 | GIL0047 | 29.2 | 0.0000 | 5.1 | 1.9 |
| RP11-65L3.2 | GIL0048 | 28.5 | 0.0777 | 1.1 | 0.7 |
| RP11-809N8.4 | GIL0049 | 26.3 | 0.0001 | 3.9 | 1.5 |
| RP11-65J3.1 | GIL0051 | 29.9 | 0.0004 | 3.4 | 1.7 |

TABLE 5-continued

| Differentially Expressed Genes in Gastrointestinal Cancer | | | | | |
|---|---|---|---|---|---|
| Gene ID | Internal ID | Avg Ct | q-value | minus log(10) q-value | Log2 ratio v. CTRL |
| RP11-533E19.7 | GIL0052 | 28.7 | 0.0012 | 2.9 | 1.1 |
| RP11-297D21.4 | GIL0053 | 27.5 | 0.0005 | 3.3 | 1.9 |
| RP11-423H2.3 | GIL0055 | 29.0 | 0.0000 | 6.4 | 1.7 |
| DNAJC9-AS1 | GIL0056 | 30.2 | 0.0000 | 5.2 | 1.5 |
| RP11-863P13.3 | GIL0057 | 28.2 | 0.0006 | 3.2 | 1.8 |
| RP11-230C9.4 | GIL0058 | 30.0 | 0.0002 | 3.8 | 1.6 |

What is claimed is:

1. A method of monitoring disease progression in a subject, the method comprising:

conducting an assay on a sample from a patient to measure expression levels of one or more long non-coding RNA (lncRNA) species selected from the group consisting of ENSG00000272288, ENSG00000111640, ENSG00000237017, ENSG00000249096, ENSG00000271870, ENSG00000272579, ENSG00000233223, ENSG00000267321, ENSG00000263065, ENSG00000228395, ENSG00000264304, ENSG00000261207, ENSG00000245060, ENSG00000228140, ENSG00000261346, ENSG00000242258, ENSG00000272462, ENSG00000225963, ENSG00000267194, ENSG00000260219, ENSG00000237424, ENSG00000249684, ENSG00000273265, ENSG00000256072, ENSG00000272955, ENSG00000251580, ENSG00000272782, ENSG00000260496, ENSG00000271122, ENSG00000223768, ENSG00000262312, ENSG00000244879, ENSG00000223396, ENSG00000257270, ENSG00000258768, ENSG00000243368, ENSG00000224888, and ENSG00000258302;

comparing the expression levels to a reference expression level to determine a differential expression of the lncRNA gene relative to a reference lncRNA expression profile; and determining disease progression of multiple sclerosis based on the differential expression of the lncRNA gene.

2. The method of claim 1, wherein measuring expression levels of a plurality of lncRNA species comprises obtaining a first and a second sample, measuring the expression levels of the one or more lncRNA, and determining the progression of the multiple sclerosis based on an increase or decrease in the differential expression of the lncRNA between the first and second samples.

3. The method of claim 1, wherein the sample is selected from the group consisting of blood, saliva, sputum, urine, semen, transvaginal fluid, cerebrospinal fluid, sweat, stool, a cell or a tissue biopsy.

4. The method of claim 1, wherein the assay comprises a reverse transcription polymerase chain reaction (RT-PCR).

5. The method of claim 1, further comprising conducting an assay on RNA from the sample to measure an expression level of a housekeeping gene and normalizing the expression level of the IncRNA gene to the expression level of the housekeeping gene.

6. The method of claim 5, wherein the housekeeping gene is selected from the group consisting of GAPDH, ACTB, B2M, 18S, and 28S.

7. The method of claim 2, wherein the patient receives a treatment for the multiple sclerosis in between collection of the first and second samples, and the method further comprises determining a therapeutic efficacy of the treatment based on the determined disease progression.

* * * * *